United States Patent
Fülöp et al.

(10) Patent No.: US 10,870,633 B2
(45) Date of Patent: Dec. 22, 2020

(54) TYPES OF C-3 SUBSTITUTED KYNURENIC ACID DERIVATIVES WITH IMPROVED NEUROPROTECTIVE ACTIVITY

(71) Applicant: SZEGEDI TUDOMÁNYEGYETEM, Szeged (HU)

(72) Inventors: Ferenc Fülöp, Szeged (HU); István Szatmári, Szeged (HU); József Toldi, Szeged (HU); László Vécsei, Szeged (HU)

(73) Assignee: SZEGEDI TUDOMÁNYEGYETEM, Szeged (HU)

( * ) Notice: Subject to any disclaimer, the term of this patent is extended or adjusted under 35 U.S.C. 154(b) by 0 days.

(21) Appl. No.: 16/082,099

(22) PCT Filed: Mar. 3, 2017

(86) PCT No.: PCT/HU2017/000014
§ 371 (c)(1),
(2) Date: Sep. 4, 2018

(87) PCT Pub. No.: WO2017/149333
PCT Pub. Date: Sep. 8, 2017

(65) Prior Publication Data
US 2019/0106409 A1    Apr. 11, 2019

(30) Foreign Application Priority Data
Mar. 4, 2016   (HU) .................................... 1600179

(51) Int. Cl.
*C07D 401/14* (2006.01)
*C07D 215/48* (2006.01)
(Continued)

(52) U.S. Cl.
CPC ......... *C07D 401/14* (2013.01); *C07D 215/48* (2013.01); *C07D 401/06* (2013.01);
(Continued)

(58) Field of Classification Search
CPC .................................................. C07D 401/14
See application file for complete search history.

(56) References Cited

U.S. PATENT DOCUMENTS

2006/0183909 A1    8/2006 Schmitt et al.

FOREIGN PATENT DOCUMENTS

EP          0303387 A1    2/1989
WO    WO-03010146 A1    2/2003
(Continued)

OTHER PUBLICATIONS

STN Chemical Database Registry entry for RN 881282-61-7, 2-Quinolinecarboxylic acid, 4-hydroxy-3-(4-morpholinylmethyl)-, ethyl, Supplier: Otava ED Entered STN: Apr. 20, 2006.*

"https://web.archive.org/web/20150905150000/http://www.otavachemicals.com/products/compound-libraries-for-hts/screening-collection-for-prompt-delivery" dated Sep. 5, 2015, accessed Oct. 17, 2019.*

Battaglia, G., et al., "Systemically Administered D-glucose Conjugates of 7-chlorokynurenic Acid Are Centrally Available and Exert Anticonvulsant Activity in Rodents," Brain Research, 860(1-2):149-156, (Mar. 2000).

Berge, S.M., et al., "Pharmaceutical Salts," Journal of Pharmaceutical Sciences 66(1):1-19, Wiley, United States (Jan. 1977).

Fulop, F., et al., "Syntheses, Transformations and Pharmaceutical Applications of Kynurenic Acid Derivatives," Current Medicinal Chemistry, 16(36):4828-4842, Bentham Science Publishers, United Arab Emirates, (2009).

(Continued)

*Primary Examiner* — David K O'Dell
(74) *Attorney, Agent, or Firm* — Sterne, Kessler, Goldstein & Fox P.L.L.C.

(57) ABSTRACT

The invention relates to C-3 substituted kynurenic acid derivatives with the general formula (I) wherein $R^1$ is $C_{1-7}$alkyl-, $R^6R^7N$—$C_{1-7}$alkyl-, $C_{6-10}$aryl-$C_{1-7}$alkyl group; $R^2$ is H or $C_{1-7}$alkyl group; or $R^1$ and $R^2$ with the nitrogen atom to which they are attached form a saturated or partially saturated 5-7 membered, optionally benzofused heterocyclic ring, optionally comprising additional N, O, S heteroatoms and optionally being substituted; $R^3$ is —OH, $C_{1-7}$alkyl-O—, —$NH_2$, $C_{1-7}$alkyl-NH—, $C_{6-10}$aryl-$C_{1-7}$alkyl-NH— or —NH—$(CH_2)_n$—$NR^8R^9$ group wherein n is an integer from 1 to 3; $R^4$ is H, $C_{1-7}$alkyl-, $C_{6-10}$aryl group or a halogen atom; $R^5$ is H or $C_{6-10}$aryl group; R6 is $C_{1-7}$alkyl group; $R^7$ is $C_{1-7}$alkyl group; or $R^6$ and $R^7$ with the nitrogen atom to which they are attached form a saturated or partially saturated 5-7 membered, optionally benzofused heterocyclic ring, optionally comprising additional N, O, S heteroatoms and optionally being substituted; $R^8$ is $C_{1-7}$alkyl group; $R^9$ is $C_{1-7}$alkyl group; $R^8$ and $R^9$ with the nitrogen atom to which they are attached form a saturated or partially saturated 5-7 membered, optionally benzofused heterocyclic ring, optionally comprising additional N, O, S heteroatoms and optionally being substituted; and stereoisomers, tautomers and salts thereof. The invention relates to the pharmaceutical preparations comprising the compounds and stereoisomers, tautomers and pharmaceutically acceptable salts. The compounds of the invention have neuroprotective activity, may be used for the prevention and treatment of neurodegeneration, and for slowing down the development of the conditions and diseases associated with a decline in cognitive abilities.

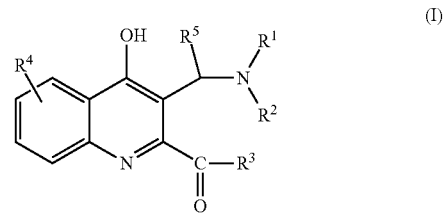

(I)

18 Claims, 4 Drawing Sheets

(51) Int. Cl.
*C07D 401/06* (2006.01)
*C07D 413/06* (2006.01)
*C07D 413/14* (2006.01)
*A61P 25/28* (2006.01)
*A61P 25/08* (2006.01)
*A61P 25/16* (2006.01)
*A61P 25/06* (2006.01)

(52) U.S. Cl.
CPC ......... *C07D 413/06* (2013.01); *C07D 413/14* (2013.01); *A61P 25/06* (2018.01); *A61P 25/08* (2018.01); *A61P 25/16* (2018.01); *A61P 25/28* (2018.01)

(56) References Cited

FOREIGN PATENT DOCUMENTS

| WO | WO-2006010967 A1 | 2/2006 |
| WO | WO-2008087461 A2 | 7/2008 |
| WO | WO-2010128345 A1 | 11/2010 |
| WO | WO-2012001438 A1 | 1/2012 |

OTHER PUBLICATIONS

Hilmas, C., et al., "The Brain Metabolite Kynurenic Acid Inhibits α7 Nicotinic Receptor Activity and Increases Non-α7 Nicotinic Receptor Expression: Physiopathological Implications," The Journal of Neuroscience, 21(19):7463-7473, Society for Neuroscience, United States, (Oct. 2001).

Lugo-Huitron, R., et al., "On the Antioxidant Properties of Kynurenic Acid: Free Radical Scavenging Activity and Inhibition of Oxidative Stress," Neurotoxicology and Teratology, 33(5):538-547, Pergamon Press, United States, (Sep.-Oct. 2011).

Marchi, M., et al., "Direct Evidence That Release-stimulating α7* Nicotinic Cholinergic Receptors Are Localized on Human and Rat Brain Glutamatergic Axon Terminals," Journal of Neurochemistry, 80(6):1071-1078, Wiley on behalf of the International Society for Neurochemistry, England, (Mar. 2002).

Nakagawa, S., et al., "A New Blood-brain Barrier Model Using Primary Rat Brain Endothelial Cells, Pericytes and Astrocytes," Neurochemistry International, 54(3-4):253-263, Pergamon Press, England, (Mar.-Apr. 2009).

Nistico, R., et al., "Neuroprotective Effect of Hydrogen Peroxide on an in Vitro Model of Brain Ischaemia," British Journal of Pharmacology, 153(5):1022-1029, Wiley, England, (Mar. 2008).

Picconi, B., et al., "Acetyl-l-carnitine Protects Striatal Neurons Against in Vitro Ischemia: the Role of Endogenous Acetylcholine," Neuropharmacology, 50(8):917-923, Pergamon Press, England, (Jun. 2006).

Prescott, C., et al., "Kynurenic Acid Has a Dual Action on AMPA Receptor Responses," Neuroscience Letters, 402(1-2):108-112, Elsevier Scientific Publishers Ireland, Ireland, (Jul. 2006).

Rozsa, E., et al., "The Janus-face Kynurenic Acid," Journal of Neural Transmission (Vienna), 115(8):1087-1091, Springer-Verlag, Austria, (Aug. 2008).

Szalardy, L., et al., "Manipulating Kynurenic Acid Levels in the Brain—on the Edge Between Neuroprotection and Cognitive Dysfunction," Current Topics in Medicinal Chemistry, 12(16):1797-1806, Bentham Science Publishers, United Arab Emirates, (2012).

Vecsei, L., et al., "Kynurenines in the CNS: Recent Advances and New Questions," Nature Reviews Drug Discovery, 12(1):64-82, Nature Publishing Group, England, (Jan. 2013).

Veszelka, S., et al., "Docosahexaenoic Acid Reduces Amyloid-β Induced Toxicity in Cells of the Neurovascular Unit," Journal of Alzheimer's Disease, 36(3):487-501, IOS Press, Netherlands, (2013).

Wang, J., et al., "Kynurenic Acid as a Ligand for Orphan G Protein-coupled Receptor GPR35," Journal of Biological Chemistry, 281(31):22021-22028, American Society for Biochemistry and Molecular Biology, United States, (Aug. 2006).

* cited by examiner

Figure 4

| 10 min | 30 min | 30 min |
|---|---|---|
| control | Der.washing in | washing off |

TYPES OF C-3 SUBSTITUTED KYNURENIC ACID DERIVATIVES WITH IMPROVED NEUROPROTECTIVE ACTIVITY

BACKGROUND OF THE INVENTION

1) Field of the invention

The invention provides new compounds and salts thereof, pharmaceutical compositions comprising the new compounds and the pharmaceutically acceptable salts thereof, and it relates to such compounds for use as medicament. The invention relates in particular to the structural analogues of kynurenic acid, which are able to prevent and treat the neurodegeneration provoking numerous diseases, and are also suitable for slowing down the conditions and diseases associated with the decline of the cognitive abilities. Furthermore, the invention relates to pharmaceutical compositions comprising such compounds and pharmaceutically acceptable salts thereof, and further to their use as medicament.

2) Description of the prior art

Neurodegeneration may happen for example if the brain is exposed to a high level of oxidative stress, mitochondrial dysfunction, inflammation, different forms of neurotoxicity (for ex-ample excitotoxicity) and/or protein (for example amyloid) abnormality. Neuroprotective agents are substances, which are able to protect the neuronal structure and/or function of the brain.

Administration of neuroprotective agents may help to minimize the effect of chronic conditions damaging the nerve cells, reducing the volume of the brain, and in the long run leading to functional disturbances. Specific examples of the factors causing neurodegeneration are: genetically coded neurodegenerative pathologies, anoxic, or haemorrhagic conditions, traumatic brain injuries, drug abuse, certain medications, schizophrenia, stroke, dementia (http://mental-healthdaily.com/2015/02/17/neuroprotective-agents).

A significant portion of the population, especially also the older generation in vulnerable physical condition, is suffering from neurodegenerative diseases [see for example Alzheimer disease (AD), Parkinson disease (PD), Hunting-ton disease (HD), amyotrophic lateral sclerosis (ALS), stroke], and from multiple sclerosis (MS) classified in the neurodegenerative/inflammatory group, as well as from epilepsy with hyperexcitability (EP) and from headache/migraine (H/M). Although there are medicinal products already authorized acting through different mechanism of action for the therapy, or in many cases only for palliative treatment of said diseases (for example: riluzole, selegiline, rasagiline, amantadine, memantine, dimethyl fumarate, levetiracetam, brivaracetam, tryptanes, etc.), but there exists a constant need for medicaments giving rise to a complete recovery, or causing less side effects (for example: heart problems, nausea, weakness, restlessness, dizziness, myoclonus, sleep disturbances, etc.).

In the pathomechanism of the above neurodegenerative symptoms partly common/similar molecular processes are involved. Although the clinical manifestation (clinical symptomatology) of the diseases mentioned is very different from each other, there are molecules, which appear and are neuroactive during the metabolic processes of the nerve tissue, and the difference in their level compared to the physiological one can be justified in numerous abnormal neural process (for example dopamine, glutamate, aspartate, quinolinic acid, free radicals, like hydroxy radicals).

The determining factor in the functioning of the nervous system is the activation and/or inhibition of the neurons (neuronal networks). The compounds with excitatory (activating) effect can potentially be "cognitive enhancers", i.e. molecules promoting the learning and memory process. Compounds inhibiting the excitatory receptors can slow down the process of neurodegeneration.

Among the neuroactive molecules affecting the above processes we can find the kynurenins, which are formed during one of the pathways of the tryptophan metabolism cited below.

Among the kynurenins (kynurenin metabolites) there are excitability enhancer, in higher doses specifically neurotoxic molecules (for example quinolinic acid), and there is one molecule, which acts as moderator to the neuronal activity, the kynurenic acid, which is specifically neuroprotective. In our recently published summary (Nat. Rev. Drug Discov. 2013, 12(1):64-82) a comprehensive study was given on the role and on the proven changes in the level of the kynurenins (kynurenic acid, quinolinic acid) during different neurological diseases, by presenting the different pathways of the tryptophan metabolism, the enzymes directing them, and the possible intermediates and final products.

The kynurenic acid acts via several mechanisms in the organism. Its endogenic glutamate receptor antagonistic effect was described, which is exerted on the glycine-binding site of the NMDA receptors as inhibitor (Curr. Top. Med. Chem., 2012, 12, 1797-1806), furthermore it has a weak antagonistic effect on the kainate and AMPA glutamate receptors.

Although the kynurenic acid has agonistic effect at low concentrations (from nanomolar to micromolar range) at the AMPA receptors, and it has antagonistic effect only in high concentrations (from micromolar to millimolar range) (Neurosci. Lett., 2006, 402, 108-112 and J. Neural. Transm., 2008, 115, 1087-1091). It was recognized that kynurenic acid is also the inhibitor of the $\alpha 7$ nicotine acetylcholine receptors ($\alpha 7$ nAChR-k) (J. Neurosci., 2001, 21, 7463-7473), whereby its neuroprotective effect via the inhibition of the glutamate release can also be justified this way (J. Neurochem., 2002, 80, 1071-1078). Kynurenic acid is the ligand of the G-protein coupled 35 receptor (GPR35), but its role in the CNS still needs further research (J. Biol. Chem., 2006, 281, 22021-22028). The observation, that it is endogenic antioxidant and a scavenger of the free radicals contributes to widening its neuroprotective spectrum (Neurotoxicol. Teratol., 2011, 33, 538-547).

The kynurenic acid is a naturally occurring molecule in the body, this fact makes likely that it has a favourable side effect profile, but at the same time the use of kynurenic acid as medicine is not an option because of the unsuitable pharmacokinetic characteristics of the compound (poor solubility, poorly crosses the blood-brain barrier, and is rapidly eliminated from the brain).

Although there were numerous attempts for raising the brain level of kynurenic acid, no official authorization is known so far for any compound, which would satisfy the demand for the specific and effective, neuroprotective drugs in the human therapy, suitable for retaining the cognitive abilities.

Some synthetic kynurenic acid derivatives, for example the 5- and/or 7-alkyl and/or halogen derivatives of the 4-oxo-1,4-dihydroquinolin-2-carboxylic acid, were reported possessing neuroprotective effect on the basis of their NMDA antagonistic activity, (EP 0 303 387 A). In order to facilitate the crossing the blood brain barrier of the 7-chlorokynurenic acid, which has proven to have neuroprotective effect, its esters with sugars (such as D-glucose, D-galactose), i.e. its pro-drugs were prepared, and their anticonvulsant properties have been described (Brain Res., 2000, 860. 149-56). The amides formed with cyclic amines from the kynurenic acid differently substituted on the aromatic ring (primarily with hydroxy group and the derivatives thereof) have proven to be analgesic (WO 2006/010967 A1). The kynurenic acid and its amides and esters (for example esters with glycerine), as free radical scavengers have proven to be suitable for the treatment of diseases of the gastrointestinal tract associated with hypermotility and inflammation, and gout and/or multiple sclerosis (WO 2008/087461 A2). In relation to the immune effect it must be highlighted that said kynurenic acid analogue inhibited the experimental intestinal inflammation and the mediators playing a role in the inflammatory processes. The use of the amides of the kynurenic acid comprising basic side-chain was also reported for the treatment of headache (WO 2010/128345 A1). The suitability of similar derivatives for the treatment of the Huntington disease has also been demonstrated (WO 2012/001438 A1).

The kynurenic acid derivatives mentioned above were not substituted in position 3, till now only one quinoline ring derivative, similar to the kynurenic acid, was described, a 3-substituted xanthurenic acid-(8-hydroxy-kynurenic acid) derivative (US 2006/0183909), and based on its dopaminergic neurotransmission modulating effect its suitability for the treatment of CNS diseases was assumed.

In the course of our work directed to the search of more effective kynurenic acid derivatives with more favourable pharmacokinetic properties, the principal aim was the preparation of new kynurenic acid derivatives substituted in position 3 and the use thereof as medicament in the prevention and treatment neurodegenerative diseases, like for example Alzheimer disease (AD), Parkinson disease (PD), Huntington disease (HD), amyotrophic lateral sclerosis (ALS), stroke, as well as multiple sclerosis (MS) classified in the neurodegenerative/inflammatory group, epilepsy with hyperexcitability (EP) and headache/migraine (H/M), and/or for slowing down the conditions and diseases associated with the decline of the cognitive abilities (for example: AD, HD, PD, ALS, MS).

Surprisingly and unexpectedly, it has been found that the new C-3 substituted kynurenic acid derivatives of the invention according to general formula (I) can cross the blood-brain barrier more easily than the known derivatives and have a structure-specific activity influencing the cortical and hippocampal activity.

The hippocampus and the cortex are especially sensitive regions of the brain tissue, which play a decisive role, in addition to the cognitive (learning and memory) functions, in the development of migraine, epilepsy and Alzheimer disease. Those kynurenic acid analogues of the invention, which have inhibitory effect, positively influence the neurodegenerative clinical patterns (AD, PD, HD, ALS, stroke, MS, EP, F). Namely, they can slow down the process of neurodegeneration with the inhibition of the excitatory receptors. At the same time, on the basis of the Janus-faced nature of the kynurenic acid (J. Neuronal. Transm. 115, 1087-1091, 2008), it can be assumed that the compounds of the invention in a concentration much lower relative to the inhibitory effect (in the nanomolar range) have an excitatory effect, and contribute to the conservation of the cognitive abilities.

SUMMARY OF THE INVENTION

The invention is directed to C-3 substituted kynurenic acid derivatives and salts thereof, to the pharmaceutical preparations containing the new compounds and their pharmaceutically acceptable salts, and to the compounds for use as medicament. The compounds of the invention are useful for the treatment and prevention of diseases and pathophysiological conditions requiring neuroprotection, and/or for braking the development of the conditions and diseases associated to the impairment of the cognitive abilities.

The invention is based on the surprising finding that crossing the blood-brain barrier of the C-3 substituted kynurenic acid derivatives characterized by general formula (I) is more favourable than that of the known derivatives, and the compounds exhibit structure-specific influence on the cortical and hippocampal activity, whereby they are useful as medicaments in the prevention and/or treatment of diseases wherein neurodegeneration is involved such as for example Alzheimer disease (AD), Parkinson disease (PD), Huntington disease (HD), amyotrophic lateralsclerosis (ALS), stroke, and multiple sclerosis (MS) classified in the neurodegenerative/inflammatory group, epilepsy with hyperexcitability (EP) and headache/migraine (H/M), and/or they can be used for slowing down the development of the conditions and diseases associated with the decline of the cognitive abilities (for example: AD, HD, PD, ALS, SM).

Since crossing through the BBB of the compounds of invention is more favourable, therefore it is expected, that they can be used in smaller doses, which may result in more favourable side effect profile, and in addition their slower metabolism can result in prolonged effect.

DETAILED DESCRIPTION OF THE INVENTION

The invention provides C-3 substituted kynurenic acid derivatives of general formula (I)

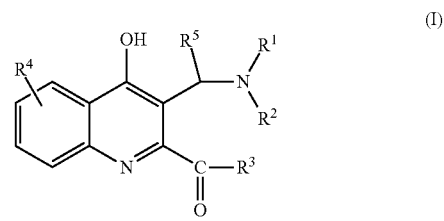

wherein
$R^1$ is $C_{1-7}$alkyl-, $R^6R^7N$—$C_{1-7}$alkyl-, $C_{6-10}$aryl-$C_{1-7}$alkyl group;
$R^2$ is H or $C_{1-7}$alkyl group; or
$R^1$ and $R^2$ with the nitrogen atom to which they are attached form a saturated or partially saturated 5-7 membered, optionally benzofused heterocyclic ring, optionally comprising additional N, O, S heteroatoms and optionally substituted with one or more $C_{1-7}$alkyl-, $C_{6-10}$aryl-$C_{1-7}$alkyl-, $C_{1-7}$alkoxy groups;
$R^3$ is —OH, $C_{1-7}$alkyl-O—, —NH$_2$, $C_{1-7}$alkyl-NH—, $C_{6-10}$aryl-$C_{1-7}$alkyl-NH— or —NH——(CH$_2$)$_n$—NR$^8$R$^9$ group wherein n is an integer from 1 to 3;
$R^4$ is H, $C_{1-7}$alkyl-, $C_{6-10}$aryl group or a halogen atom;
$R^5$ is H or $C_{6-10}$aryl group;
$R^6$ is $C_{1-7}$alkyl group;
$R^7$ is $C_{1-7}$alkyl group; or $R^6$ and $R^7$ with the nitrogen atom to which they are attached form a saturated or partially saturated 5-7 membered, optionally benzofused heterocyclic ring, optionally comprising additional N, O, S heteroatoms and optionally substituted with one or more $C_{1-7}$alkyl-, $C_{6-10}$aryl-$C_{1-7}$alkyl-, $C_{1-7}$alkoxy groups;

$R^8$ is $C_{1-7}$alkyl group;

$R^9$ is $C_{1-7}$alkyl group; or $R^8$ and $R^9$ with the nitrogen atom to which they are attached form a saturated or partially saturated 5-7 membered, optionally benzofused heterocyclic ring, optionally comprising additional N, O, S heteroatoms and optionally substituted with one or more $C_{1-7}$alkyl-, $C_{6-10}$aryl-$C_{1-7}$alkyl-, $C_{1-7}$alkoxy groups;

and stereoisomers, tautomers and salts thereof.

The invention further relates to pharmaceutical compositions comprising the compounds of general formula (I) as defined above, and stereoisomers, tautomers and pharmaceutically acceptable salts thereof, and one or more pharmaceutically acceptable carrier and/or adjuvant.

The invention further relates to the use of the compounds of general formula (I) defined above as medicament.

DESCRIPTION OF FIGURES

FIG. 4 A depiction of a 10 minute control phase, followed by washing a derivative of the invention for 30 minutes, and then an additional 30 minute washing off phase.

ABBREVIATIONS

Figure 1:
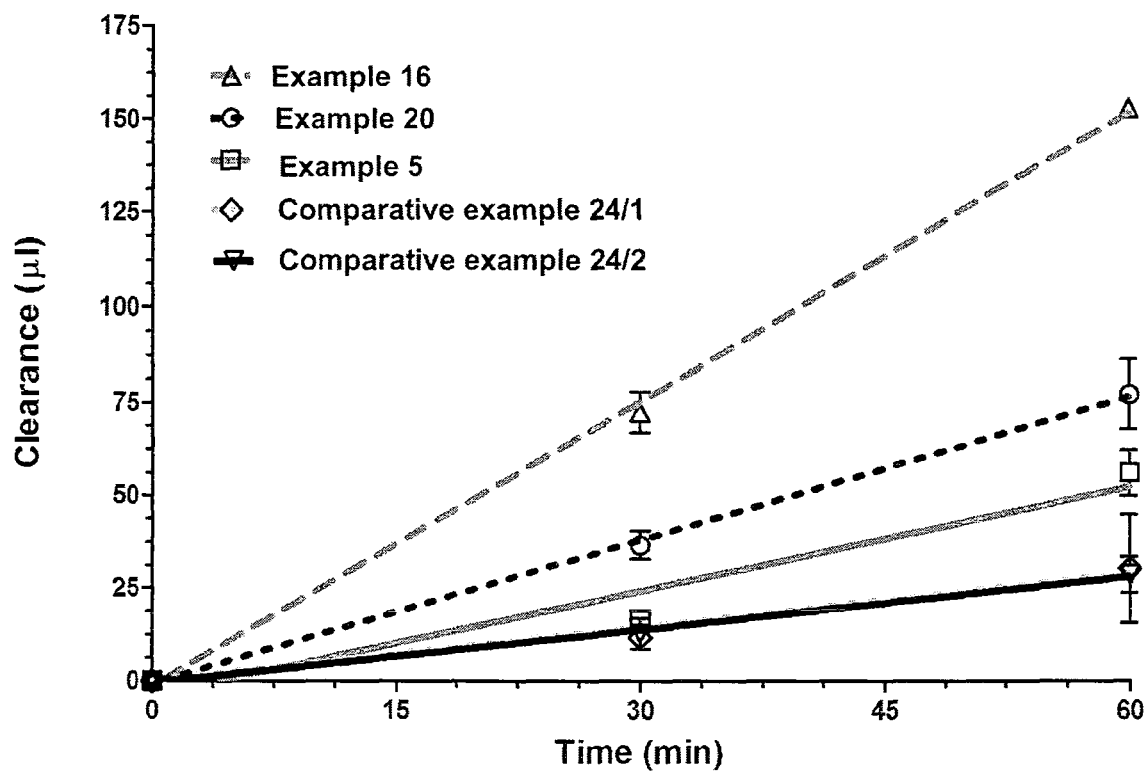
FIG. 1 The bidirectional clearance values of compounds of Examples 24/1, 24/2 and 5, 16 and 20 on blood-brain barrier model (n=6). A-B direction: left-hand graph; B-A direction: right-hand graph.
Figure 1:
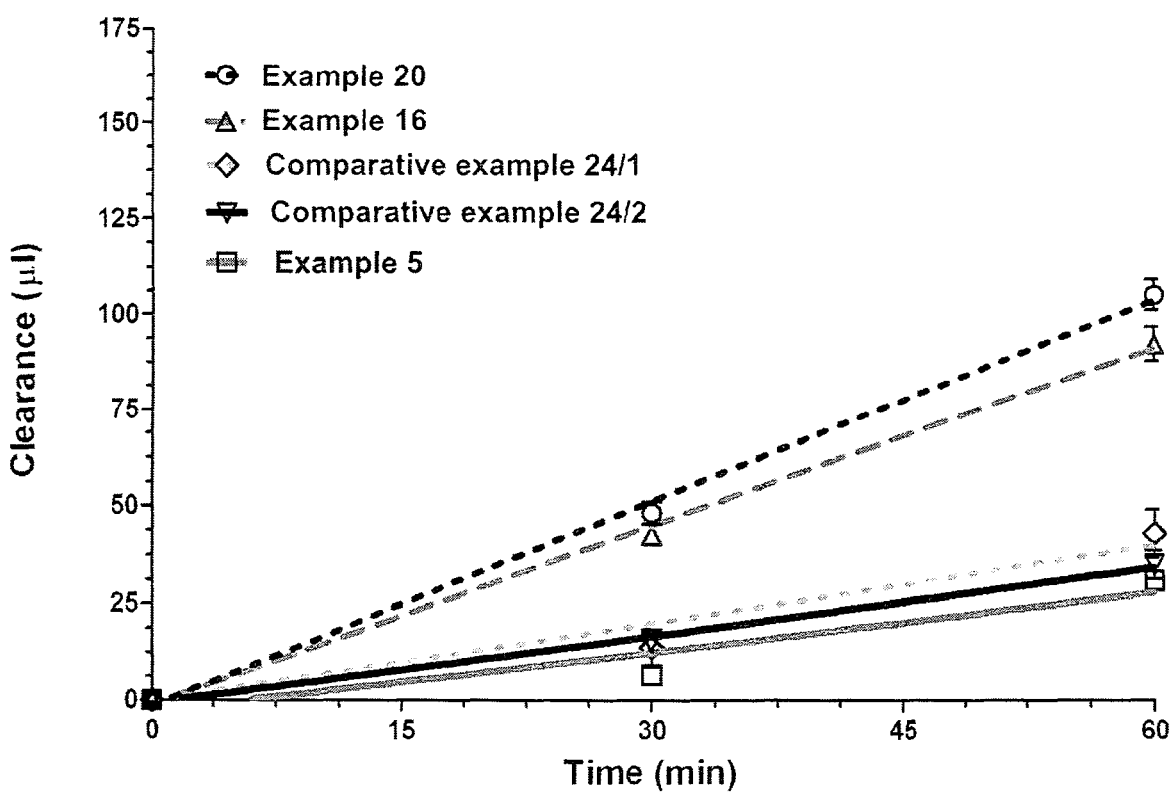

AD Alzheimer disease
PD Parkinson disease
HD Huntington disease
ALS amyotrophic lateral sclerosis
MS multiple sclerosis
EP epilepsy
P pain
M migraine
aCSF artificial cerebrospinal fluid,
AB "from the blood to the brain"
BA "from the brain to the blood"
$P_{app}$, apparent permeability coefficient
fEPSP excitatory postsynaptic field potential
α7nACh receptor α7 nicotine acetylcholine receptors
(CSD) cortical spreading depolarization
NTG nitroglycerine
SUMA sumatryptan
BBB Blood-Brain Barrier

Definitions

The term "alkyl" as used herein refers to an optionally substituted straight chain, or optionally substituted branched chain saturated alkyl hydrocarbon radical having from one to seven carbon atoms. Examples of alkyl radicals include methyl-, ethyl-, n-propyl-, isopropyl-, n-butyl-, isobutyl-, sec-butyl-, tert-butyl-, tert-amyl-, pentyl-, hexyl-radicals and the like.

The term "alkoxy" as used herein refers to the alkyl-O-groups, wherein the alkyl term is defined as above. Examples of alkoxy radicals include methoxy-, ethoxy-, n-propoxy-, isopropoxy-, n-butoxy-, iso-butoxy-, sec-butoxy-, tert-butoxy-groups and the like.

The term "aryl" as used herein refers to an aryl group having six to ten carbon atoms in the cyclic backbone, for example phenyl and naphthyl.

The term "arylalkyl" as used herein refers to an alkyl radical, in which at least one hydrogen is replaced with an aryl radical defined above, for example benzyl, 2-phenyl-ethyl and the like.

The term "halogen" as used herein refers to fluoro, chloro, bromo, and iodo.

The term "heterocyclic" as used herein refers to an optionally substituted and fused, and in heterocyclic part saturated or partly saturated group containing from five to seven ring atoms, in which one ring atom is nitrogen, and optionally contains additional heteroatoms too, like for example oxygen, nitrogen and sulphur atom, and which can optionally be benzofused, for example, without the intention of limitation, piperidyl, piperazinyl, methyl-piperazinyl, 1,2,3,4-tetrahydroisoquinolinyl, 1,2,3,4-tetrahydro-6,7-dimethoxy-isoquinolinyl, tetrahydrobenzazepinyl, pyrrolidinyl, morpholinyl and the like. Optionally the heterocycles may be substituted with alkyl or alkoxy group, as it is defined above.

The "optionally substituted" groups may be substituted or unsubstituted.

Some compounds of the invention may contain one or more chiral centres, and therefore may exist in enantiomeric or diastereoisomeric forms. The scope covered by the present invention is intended to include all isomers per se, and the mixture of the cis and trans isomers, the mixture of diastereomers and the racemic mixture of enantiomers (optical isomers) too. In addition it is possible to use well known techniques for the separation of the different forms, and the invention may include the purified or enriched forms of a given enantiomer or diastereomer.

According to the lactam-lactim tautomerism the kynurenic acid is known as 4-hydroxy-quinoline-2-carboxylic acid, or 1H-quinoline-4-one-2-carboxylic acid, which equilibrium forms differ in the position of a proton and a double bond, and the same relates to the compounds of the invention too.

Conditions requiring neuroprotection are, for example Alzheimer disease (AD), Parkinson disease (PD), Huntington disease (HD), amyotrophic lateral sclerosis (ALS), stroke, and multiple sclerosis (MS) classified in the neurodegenerative/inflammatory group, epilepsy with hyperexcitability (EP) and the headache/migraine (H/M).

Neurodegenerative diseases, which are characterized by the progressive dysfunction of the nervous system, especially Alzheimer disease, frontotemporal dementia, Lewy body dementia, corticobasal degeneration, progressive supranuclear palsy, prion diseases, multiple system atrophy, ALS (also known as Lou Gehrig's disease), Parkinson disease, Huntington disease, neurodegenerative diseases associated with polyglutamine-repeat, multiple sclerosis, hereditary spastic paraparesis, spinocerebellar atrophy, diseases associated with brain tumour, degenerative nervous system diseases, encephalitis, epilepsy, genetic brain diseases, head and brain malformations, hydrocephalus, stroke and associated diseases, prion diseases, amyloidosis, Friedreich's ataxia, metabolic diseases (for example diabetes), diseases caused by toxins, Charcot-Marie-Tooth disease and others.

Conditions and diseases associated with the decline of the cognitive abilities are for example Alzheimer disease (AD), Parkinson disease (PD), Huntington disease (HD), amyotrophic lateral sclerosis (ALS), stroke, and the multiple sclerosis (MS) classified in the neurodegenerative/inflammatory group, the epilepsy with hyperexcitability (EP).

The "therapeutically/pharmaceutically suitable salt" may be prepared from any compound of the invention having salt-forming, for example basic or acidic functionality. Pharmaceutically suitable salt may be prepared with organic or inorganic acids or bases. The compounds of the invention which have one or more basic functional group (for example amino, alkyl-amino) can form pharmaceutically suitable salt with pharmaceutically suitable organic or inorganic salts. These salts can be prepared in situ in the course of the final isolation or purification of the compounds of the invention, or by separately reacting the purified compounds of the invention in the form of free base with suitable organic or inorganic acids, and by separating the salt generated this way. Suitable salts may be for example: acetate, adipate, alginate, aspartate, benzoate, benzenesulfonate, bisulphate, butyrate, citrate, camphorate, camphorsulphonate, cyclopentanepropionate, digluconate, dodecylsulphate, ethanesulphonate, formate, fumarate, glucoheptanoate, glycerophosphate, glycolate, hemisulphate, heptanoate, hexanoate, hydrochloride, hydrobromide, hydroiodide, 2-hydroxy-ethanesulphonate, lactate, maleate, malonate, methanesulphonate, 2-naphthalene sulfonate, nicotinate, nitrate, oxalate, palmoate, pectinate, persulfate, 3-phenyl-propionate, phosphate, picrate, pivalate, propionate, salicylate, succinate, sulphate, tartrate, thiocyanate, tosylate, and undecanoate. Other acids, like for example the oxalic acid, which in themselves are pharmaceutically unsuitable, can be used as intermediates in the course of the preparation of suitable salts for the preparation of pharmaceutically suitable compounds of the invention or their acid addition salts. The compounds of the invention which have one or more acidic functional group can form pharmaceutically suitable salt with pharmaceutically suitable bases. In this case the term "pharmaceutically suitable salt" relates to the base addition salts of the invention, formed with relatively non-toxic inorganic and organic bases. These salts can similarly be prepared in situ in the course of the final isolation or purification of the compounds of the invention, or by separately reacting the purified compounds of the invention in the form of free acid with suitable organic or inorganic base, for example with pharmaceutically suitable metal-cation hydroxide, carbonate or bicarbonate, with ammonia or pharmaceutically suitable organic primary, secondary or tertiary amine. The pharmaceutically suitable cations include the alkali or alkaline earth metal salts, like for example the lithium, sodium, calcium, magnesium and aluminium salts and the like. Illustrative examples for some suitable base are the sodium hydroxide, potassium hydroxide, choline hydroxide, sodium carbonate, tetrabutylammonium hydroxide and the like. The representative organic amines which are useful in the preparation of base addition salts are the ethylamine, diethylamine, ethylene diamine, ethanolamine, diethanolamine, piperazine and the like. The invention also anticipates the quaternization of any kind of nitrogen containing groups of the compounds presented here. Product soluble in water or in oil can be obtained with such quaternization (see for example: Berge et al. "Pharmaceutical Salts", J. Pharm. Sci. 1977, 66.1-19).

It is obvious that the reference to a salt includes its solvent containing or crystalline forms, especially the solvates and the polymorphs. The solvates contain solvent in stoichiometric or non-stoichiometric amount, and are often formed in the course of the crystallization with such, therapeutically suitable solvents as the water, ethanol and the like. Hydrates form when the solvent is water, or alcoholates form when the solvent is alcohol. The polymorphs include the different crystalline arrangement of a compound with the same elemental composition. Polymorphs usually have different X-ray diffraction pattern, infrared spectrum, melting point, specific gravity, hardness, crystalline form, optical and electric properties, stability and solubility. Different factors like the recrystallization solvent, rate of crystallization, and storage temperature may give rise the dominance of a single crystalline form.

The term "pharmaceutically suitable carrier and/or adjuvant" as used herein refers to a pharmaceutically accepted substance, composition or carrier, like for example liquid or solid filler, diluent, adjuvant, solvent, encapsulating material which is taking part in carrying or transportation of said agent from one organ or body part to another organ or body part. Each carrier should be "acceptable" in a sense, that it is compatible with the other components of the formulation, and it is not harmful for the patient. Some examples of the substances, without the intention of limitation, which can serve as pharmaceutically suitable carriers: sugars, like for example lactose, glucose and saccharose; starches, like for example the corn starch and potato starch; cellulose and derivatives thereof, like for example sodium carboxymethyl cellulose, ethyl cellulose and cellulose acetate; tragacanth powder, malt, gelatine, talc, excipients, like for example the cocoa butter and suppository waxes, oils, like for example the peanut oil, cottonseed oil, safflower oil, sesame oil, olive oil, corn oil and soybean oil; glycols, like propylene glycol, polyols, like for example glycerine, sorbitol, mannitol and polyethylene glycol; esters like the ethyl oleate and ethyl laurate; agar; buffer substances, like for example magnesium hydroxide and aluminium hydroxide, alginic acid, pyrogen-free water, isotonic saline, Ringer's solution, ethylalcohol, phosphate buffer solution, and other non-toxic substances, used in the pharmaceutical compositions, compatible with the pharmaceuticalcomposition.

The term "excipient" relates to a neutral substance, which is added to the pharmaceutical preparation, to facilitate the application of a compound. Some examples for the excipients, without the intention of limitation, calcium carbonate, calcium phosphate, different kind of sugars and starch, cellulose derivatives, gelatine, vegetable oils and polyethylene glycols.

The term "therapeutically effective amount" relates to a quantity, which is capable of eliciting a therapeutic and/or prophylactic effect. Of course, the specified dose of the compound which is used according to the present invention to achieve therapeutic and/or prophylactic effect will be determined by the particular circumstances specific to each case, including for example the administration of the specified compound, the route of administration, the pathophysiological condition treated, and the treated patient. A typical daily dose (in a single or in divided dose) extends from about 0.01 mg/kg body weight to 50-100 mg/kg body weight. Preferred daily doses generally will be from about 0.05 mg/kg to about 20 mg/kg and ideally extend from about 0.1 mg/kg to 10 mg/kg. The factors like the clearance rate, half-life and maximum tolerated dose (MTD) have not been determined yet, but these can be defined by a person with a general expertise, using standard procedures.

The pharmaceutical compositions of the invention may be administered orally, parenterally, with spray inhalation, locally, rectally, nasally, buccally, vaginally, or with an implanted dispenser intrathecally and intracerebrally.

The term "parenteral" as used herein relates to the subcutaneous, intracutaneous, intravenous, intramuscular, intraarticular, intrasynovial, intrasternal, intrathecal, intralesional and intracranial injection or infusion techniques.

The pharmaceutical preparations of the invention may be used orally, in any orally acceptable dosage form, including, without the intention of limitation, the capsules, tablets, aqueous suspensions and the solutions. In case of orally applicable tablets the frequently used carriers include lactose and corn starch. Lubricants such as magnesium stearate, are also typically added. Lactose and the dried corn starch are useful diluents for the orally applicable capsule form. When aqueous suspensions and solutions and propylene glycol are administered orally, the active ingredient is combined with emulsifying and suspending agents. Certain sweeteners and/or flavouring and/or colouring agents may also be added if necessary.

The preparations of the invention may be prepared with methods known per se in relation to the preparation of the pharmaceutical preparation, by mixing the active ingredient and the suitable carriers and/or excipients. The preparations generally contain 0.5-99.5% active compound.

Compounds of the Invention

The invention relates to the new C-3 substituted kynurenic acid derivatives according to general formula (I)

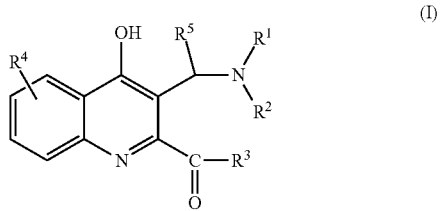

(I)

wherein
$R^1$ is $C_{1-7}$alkyl-, $R^6R^7N$—$C_{1-7}$alkyl-, $C_{6-10}$aryl-$C_{1-7}$alkyl group;
$R^2$ is H or $C_{1-7}$alkyl group; or
$R^1$ and $R^2$ with the nitrogen atom to which they are attached form a saturated or partially saturated 5-7 membered, optionally benzofused heterocyclic ring, optionally comprising additional N, O, S heteroatoms and optionally substituted with one or more $C_{1-7}$alkyl-, $C_{6-10}$aryl-$C_{1-7}$alkyl-, $C_{1-7}$alkoxy groups;
$R^3$ is —OH, $C_{1-7}$alkyl-O—, —$NH_2$, $C_{1-7}$alkyl-NH—, $C_{6-10}$aryl-$C_{1-7}$alkyl-NH— or —NH——$(CH_2)_n$—$NR^8R^9$ group wherein n is an integer from 1 to 3;
$R^4$ is H, $C_{1-7}$alkyl-, $C_{6-10}$aryl group or a halogen atom;
$R^5$ is H or $C_{6-10}$aryl group;
$R^6$ is $C_{1-7}$alkyl group;
$R^7$ is $C_{1-7}$alkyl group; or
$R^6$ and $R^7$ with the nitrogen atom to which they are attached form a saturated or partially saturated 5-7 membered, optionally benzofused heterocyclic ring, optionally comprising additional N, O, S heteroatoms and optionally substituted with one or more $C_{1-7}$alkyl-, $C_{6-10}$aryl-$C_{1-7}$alkyl-, $C_{1-7}$alkoxy groups;
$R^8$ is $C_{1-7}$alkyl group;
$R^9$ is $C_{1-7}$alkyl group; or
$R^8$ and $R^9$ with the nitrogen atom to which they are attached form saturated or partially saturated 5-7 membered, optionally benzofused heterocyclic ring, optionally comprising additional N, O, S heteroatoms and optionally substituted with one or more $C_{1-7}$alkyl-, $C_{6-10}$aryl-$C_{1-7}$alkyl-, $C_{1-7}$alkoxy groups;
and stereoisomers, tautomers and salts thereof.

In some embodiments
$R^1$ is $R^6R^7N$—$C_{1-7}$alkyl-,
$R^2$ is H or
$R^1$ and $R^2$ with the nitrogen atom to which they are attached form a saturated or partially saturated 5-6 membered, optionally benzofused heterocyclic ring, optionally comprising additional N, O, S heteroatoms and optionally substituted with one or more $C_{1-7}$alkyl-, $C_{6-10}$aryl-$C_{1-7}$alkyl-, $C_{1-7}$alkoxy groups;
$R^3$ is —OH, $C_{1-7}$alkyl-O—, —$NH_2$, $C_{1-7}$alkyl-NH—, $C_{6-10}$aryl-$C_{1-7}$alkyl-NH— or —NH——$(CH_2)_n$—$NR^8R^9$ group wherein n is an integer from 1 to 3;
$R^4$ is H, $C_{1-7}$alkyl-, $C_{6-10}$aryl group or a halogen atom;
$R^5$ is H or $C_{6-10}$aryl group;
$R^6$ and $R^7$ with the nitrogen atom to which they are attached form a saturated or partially saturated 5-6 membered, optionally benzofused heterocyclic ring, optionally comprising additional N, O, S heteroatoms and optionally substituted with one or more $C_{1-7}$alkyl-, $C_{6-10}$aryl-$C_{1-7}$alkyl-, $C_{1-7}$alkoxy groups;
$R^8$ and $R^9$ with the nitrogen atom to which they are attached form a saturated or partially saturated 5-6 membered, optionally benzofused heterocyclic ring, optionally comprising additional N, O, S heteroatoms and optionally substituted with one or more $C_{1-7}$alkyl-, $C_{6-10}$aryl-$C_{1-7}$alkyl-, $C_{1-7}$alkoxy groups;
and stereoisomers, tautomers and salts thereof.

In a preferred embodiment
$R^1$ and $R^2$ with the nitrogen atom to which they are attached form saturated or partially saturated 6 membered, benzofused heterocyclic ring, optionally substituted with one or more $C_{1-7}$alkyl-, $C_{6-10}$aryl-$C_{1-7}$alkyl-, $C_{1-7}$alkoxy groups;
$R^3$ is —OH, $C_{1-7}$alkyl-O—, —$NH_2$, $C_{1-7}$alkyl-NH—, $C_{6-10}$aryl-$C_{1-7}$alkyl-NH— or —NH——$(CH_2)_n$—$NR^8R^9$ group wherein n is an integer from 1 to 3;
$R^4$ is H, $C_{1-7}$alkyl-, $C_{6-10}$aryl group or a halogen atom;
$R^5$ is H or $C_{6-10}$aryl group;
$R^8$ and $R^9$ with the nitrogen atom to which they are attached form a saturated or partially saturated 5-6 membered, optionally benzofused heterocyclic ring, optionally comprising additional N, O, S heteroatoms and optionally substituted with one or more $C_{1-7}$alkyl-, $C_{6-10}$aryl-$C_{1-7}$alkyl-, $C_{1-7}$alkoxy groups;
and stereoisomers, tautomers and salts thereof.

In another preferred embodiment
$R^1$ is morpholino-ethyl-,
$R^2$ is H;
$R^3$ is —OH, $C_{1-7}$alkyl-O—, —$NH_2$, $C_{1-7}$alkyl-NH—, $C_{6-10}$aryl-$C_{1-7}$alkyl-NH— or —NH——$(CH_2)_n$—$NR^8R^9$ group wherein n is an integer from 1 to 3;
$R^4$ is H, $C_{1-7}$alkyl-, $C_{6-10}$aryl group or a halogen atom;
$R^5$ is H or $C_{6-10}$aryl group;
$R^8$ is $C_{1-7}$alkyl group;
$R^9$ is $C_{1-7}$alkyl group; or
$R^8$ and $R^9$ with the nitrogen atom to which they are attached form a saturated or partially saturated 5-6 membered, optionally benzofused heterocyclic ring, optionally comprising additional N, O, S heteroatoms and optionally substituted with one or more $C_{1-7}$alkyl-, $C_{6-10}$aryl-$C_{1-7}$alkyl-, $C_{1-7}$alkoxy groups;
and stereoisomers, tautomers and salts thereof.

TABLE I

Examples of the compounds according to general formula (I)

| Examples | Structure | Name |
|---|---|---|
| 1 | 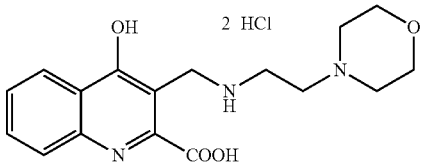 [SMILES: O=C(O)c1nc2ccccc2c(O)c1CNCCN1CCOCC1 ; Cl] | 3-((2-morpholinoethylamino)methyl)-4-hydroxyquinoline-2-carboxylic acid dihydrochloride |
| 2 | 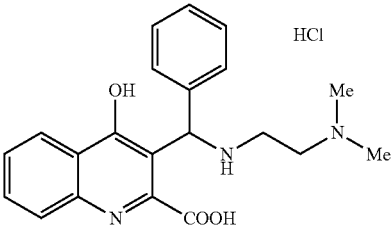 [SMILES: CN(C)CCNC(c1ccccc1)c1c(C(=O)O)nc2ccccc2c1O ; Cl] | 3-((2-(dimethylamino)ethyl-amino)(phenyl)methyl)-4-hydroxyquinoline-2-carboxylic acid dihydrochloride |
| 3 | 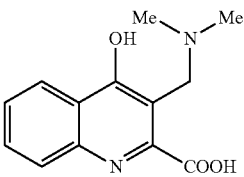 [SMILES: CN(C)Cc1c(C(=O)O)nc2ccccc2c1O] | 3-((dimethylamino)methyl)-4-hydroxyquinoline-2-carboxylic acid |
| 4 | 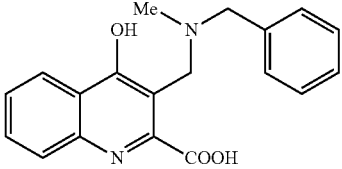 [SMILES: CN(Cc1ccccc1)Cc1c(C(=O)O)nc2ccccc2c1O] | 3-((benzylmethylamino)methyl)-4-hydroxyquinoline-2-carboxylic acid |
| 5 | 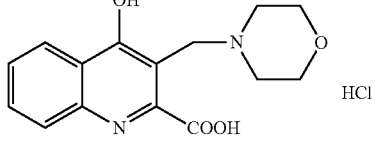 | 4-hydroxy-3-(morpholinomethyl)quinoline-2-carboxylic acid hydrochloride |
| 6 | 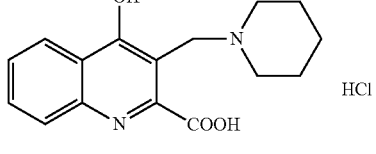 | 4-hydroxy-3-((piperidin-1-yl)methyl)quinoline-2-carboxylic acid hydrochloride |
| 7 | 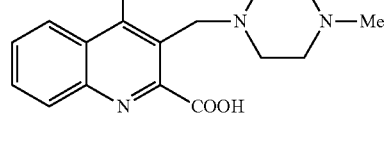 | 4-hydroxy-3-((4-methylpiperazin-1-yl)methyl)quinoline-2-carboxylic acid |
| 8 | 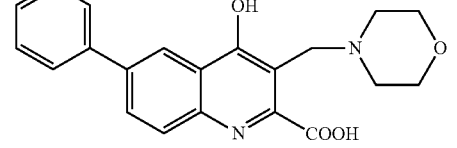 | 4-hydroxy-3-(morpholinomethyl)-6-phenylquinoline-2-carboxylic acid |

TABLE I-continued

Examples of the compounds according to general formula (I)

| Examples | Structure | Name |
|---|---|---|
| 9 | 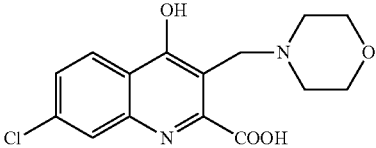 [SMILES: O=C(O)c1nc2cc(Cl)ccc2c(O)c1CN1CCOCC1] | 7-chloro-4-hydroxy-3-(morpholinomethyl)quinoline-2-carboxylic acid |
| 10 | 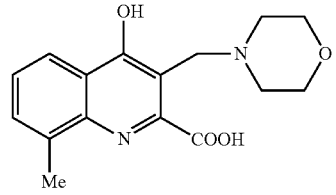 [SMILES: Cc1cccc2c(O)c(CN3CCOCC3)c(C(=O)O)nc12] | 4-hydroxy-8-methyl-3-(morpholinomethyl)quinoline-2-carboxylic acid |
| 11 | 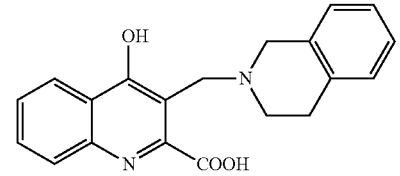 [SMILES: O=C(O)c1nc2ccccc2c(O)c1CN1CCc2ccccc2C1] | 3-((1,2,3,4-tetrahydroisoquinolin-2-yl)methyl)-4-hydroxyquinoline-2-carboxylic acid |
| 12 | 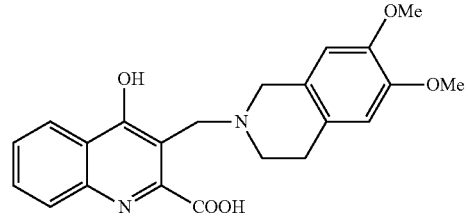 [SMILES: COc1cc2c(cc1OC)CN(Cc1c(C(=O)O)nc3ccccc3c1O)CC2] | 3-((1,2,3,4-tetrahydro-6,7-dimethoxyisoquinolin-2-yl)methyl)-4-hydroxyquinoline-2-carboxylic acid |
| 13 | 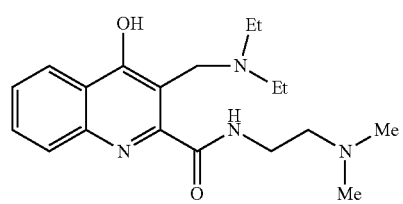 [SMILES: CCN(CC)Cc1c(C(=O)NCCN(C)C)nc2ccccc2c1O] | 3-((diethylamino)methyl)-N-(2-(dimethylamino)ethyl)-4-hydroxyquinoline-2-carboxamide |
| 14 | 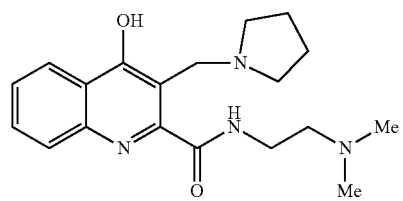 [SMILES: CN(C)CCNC(=O)c1nc2ccccc2c(O)c1CN1CCCC1] | N-(2-(dimethylamino)ethyl)-4-hydroxy-3-((pyrrolidin-1-yl)methyl)quinoline-2-carboxylic acid amide |
| 15 | 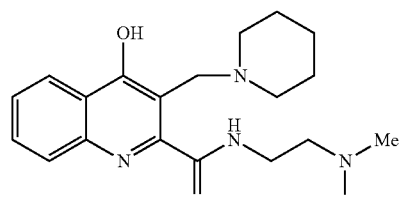 | N-(2-(dimethyl amino)ethyl)-4-hydroxy-3-((piperidine-1-yl)methyl)quinoline-2-carboxamide |

TABLE I-continued

Examples of the compounds according to general formula (I)

| Examples | Structure | Name |
| --- | --- | --- |
| 16 | 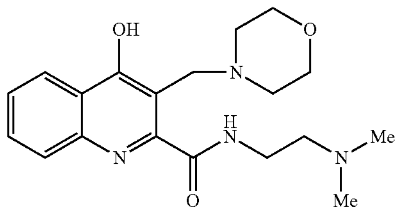 [SMILES: CN(C)CCNC(=O)c1nc2ccccc2c(O)c1CN1CCOCC1] | N-(2-(dimethylamino)ethyl)-4-hydroxy-3-(morpholinomethyl)quinoline-2-carboxamide |
| 17 | 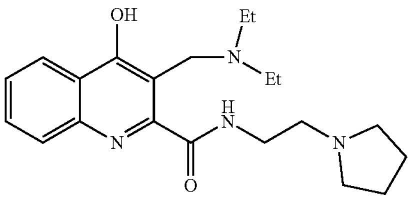 [SMILES: CCN(CC)Cc1c(C(=O)NCCN2CCCC2)nc2ccccc2c1O] | 3-((diethylamino)methyl)-4-hydroxy-N-(2-(pyrrolidin-1-yl)ethyl)quinoline-2-carboxamide |
| 18 | 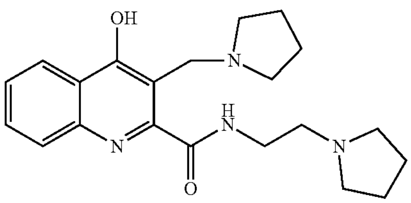 [SMILES: O=C(NCCN1CCCC1)c1nc2ccccc2c(O)c1CN1CCCC1] | 4-hydroxy-N-(2-(pyrrolidin-1-il)ethyl)-3-((pyrrolidin-1-yl)methyl)quinoline-2-carboxamide |
| 19 | 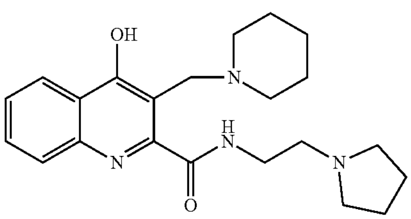 [SMILES: O=C(NCCN1CCCC1)c1nc2ccccc2c(O)c1CN1CCCCC1] | 4-hydroxy-3-((piperidin-1-yl)methyl)-N-(2-(pyrrolidin-1-il)ethyl)quinoline-2-carboxamide |
| 20 | 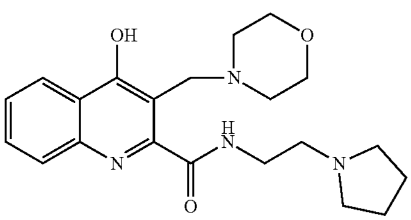 [SMILES: O=C(NCCN1CCCC1)c1nc2ccccc2c(O)c1CN1CCOCC1] | 4-hydroxy-3-(morpholinomethyl)-N-(2-(pyrrolidin-1-yl)ethyl)quinoline-2-carboxamide |
| 21 | 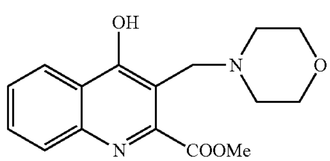 [SMILES: COC(=O)c1nc2ccccc2c(O)c1CN1CCOCC1] | 4-hydroxy-3-(morpholinomethyl)quinoline-2-carboxylic acid methyl ester |
| 22 | 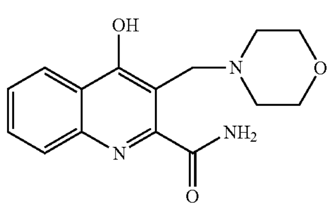 [SMILES: NC(=O)c1nc2ccccc2c(O)c1CN1CCOCC1] | 4-hydroxy-3-(morpholinomethyl)quinoline-2-carboxamide |

TABLE I-continued

Examples of the compounds according to general formula (I)

| Examples | Structure | Name |
|---|---|---|
| 23 | 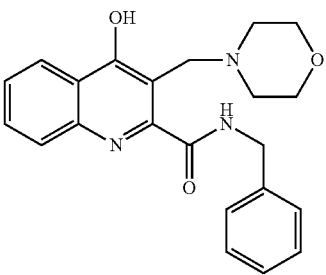 [SMILES: O=C(NCc1ccccc1)c1nc2ccccc2c(O)c1CN1CCOCC1] | N-benzyl-4-hydroxy-3-(morpholinomethyl)quinoline-2-carboxamide |

Selected compounds according to invention include, without the invention be limited to these, the compounds according to examples 5, 11, 12, 16, 17, 18. and 20.

EXAMPLES

The following examples are meant to illustrate the invention without altering its essence, or restrict the scope of the claims.

Preparation of the Compounds of the Invention

The compounds according to general formula (I) may be prepared by using classical techniques (Tetrahedron. 2013, 69, 1255-1278). As an example, the compounds of the invention may be prepared with the procedures presented on FIGS. 1, 2 and 3.

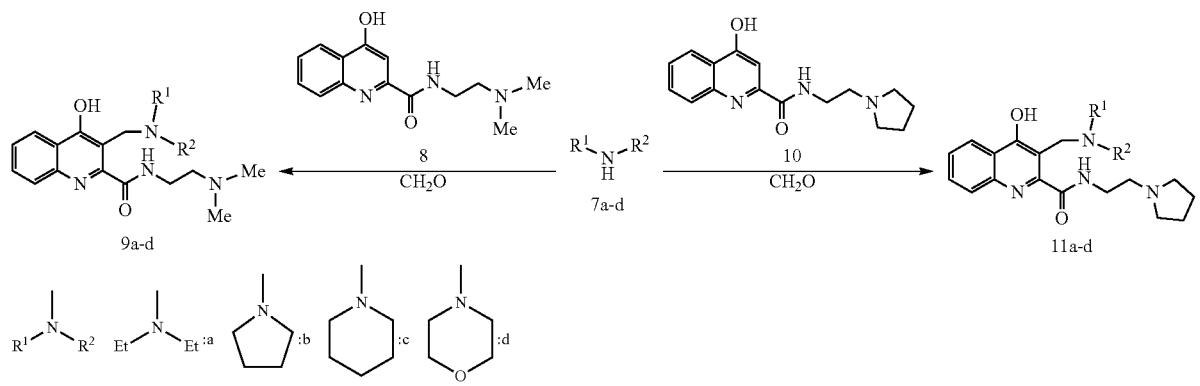

Figure 2

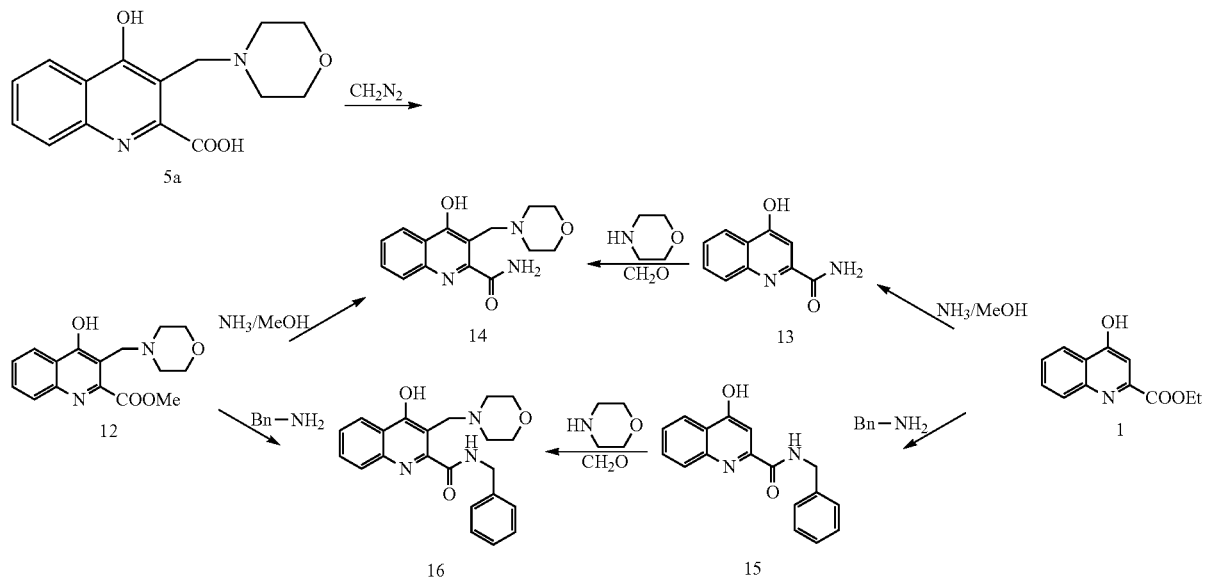

Figure 3

As it may be realized by a skilled practitioner, these processes are not the only possible methods of production, with which the discussed and claimed compounds may be prepared. Additional methods will also be obvious for people skilled in the art.

Preferably, these compounds can be readily prepared from starting materials commercially available. Otherwise preparation of the compounds is feasible on the basis of the technical literatures cited, or as described in the present invention.

The compounds of the invention were characterized with $^1$H NMR data (on 400 MHz Bruker spectrophotometer, recorded in deuterated solvent), and/or with the melting point values.

Example 1 3-((2-morpholinoethylamino)methyl)-4-hydroxyquinoline-2-carboxylic acid dihydrochloride 4-Hydroxyquinoline-2-carboxylic acid ethyl ester (A, 326 mg, 1.5 mmol), 2-morpholinoethylamine (260 mg, 2.0 mmol), and formalin (22%, 410 mg, 3.0 mmol) were placed in a 50 ml round bottom flask. The mixture was refluxed in 30 ml 1,4-dioxane for 5 hours. After the evaporation of the solvent the residue was dissolved into 40 ml water, and extracted with 3×30 ml dichloromethane. The collected organic phase was dried (Na$_2$SO$_4$), the solvent was removed by evaporation, and the residue was crystallized from n-hexane:EtOAc mixture.

For the isolation of the hydrochloride salt compound 1 was taken into 15 ml EtOH, and 0.15 ml (1.0 mmol) HCl/EtOH (22%) solution was added to the mixture. The solvent was removed by evaporation, and the residue was crystallized from 10 ml Et$_2$O.

Yield: 473 mg (78%); M.p. 300-303° C. $^1$H NMR (D$_2$O); 3.11-3.42 (2H, m); 3.54 (2H, t, J=5.6 Hz); 3.52-3.87 (4H, m); 4.01-4.20 (4H, m); 4.33 (2H, s); 7.43 (1H, t, J=7.7 Hz); 7.57 (1H, d, J=7.8 Hz); 7.72 (1H, t, J=8.1 Hz); 8.04 (1H, d, J=8.7 Hz)

Example 2 3-((2-(dimethylamino)ethylamino)(phenyl)methyl)-4-hydroxyquinoline-2-carboxylic acid dihydrochloride Preparation starting from 4-hydroxyquinoline-2-carboxylic acid (A, 326 mg, 1.5 mmol), N,N-dimethylethylene diamine (176 mg, 2.0 mmol) and benzaldehyde (318 mg, 3.0 mmol), according to example 1.

Yield: 487 mg (74%); M.p. 193-195° C. $^1$H NMR (D$_2$O); 2.74 (3H, s); 2.83 (3H, s); 2.95-3.05 (1H, m); 3.09-3.2 (1H, m); 3.55-3.65 (1H, m); 3.91-4.01 (1H, m); 5.63 (1H, s); 7.23-7.31 (2H, m); 7.36-7.49 (4H, m); 7.68-7.77 (2H, m); 8.06 (1H, d, J=8.5 Hz).

Example 3 3-((dimethylamino)methyl)-4-hydroxyquinoline-2-carboxylic acid

Preparation starting from 4-hydroxyquinoline-2-carboxylic acid (A, 326 mg, 1.5 mmol), dimethylamine (88 mg, 2.0 mmol) and formaldehyde (22%, 410 mg, 3.0 mmol) according to example 1.

Yield: 303 mg (82%); M.p. 246-249° C. $^1$H NMR (DMSO); 2.73 (3H, s); 4.33 (2H, s); 7.34 (1H, t, J=7.7 Hz); 7.66 (1H, t, J=7.8 Hz); 7.98 (1H, d, J=8.1 Hz); 8.09 (1H, d, J=7.9 Hz); 11.05 (1H, brs); 11.73 (1H, brs)

Example 4 3-((benzylmethylamino)methyl)-4-hydroxyquinoline-2-carboxylic acid Preparation starting from 4-hydroxyquinoline-2-carboxylic acid (A, 326 mg, 1.5 mmol), N-benzyl methylamine (242 mg, 2.0 mmol) and formaldehyde (22%, 410 mg, 3.0 mmol) according to example 1.

Yield: 411 mg (85%); M.p. 235-237° C. $^1$H NMR (DMSO); 2.48 (3H, s); 4.32 (2H, s); 4.41 (2H, s); 7.18-7.77 (7H, m); 7.86-8.18 (2H, m); 11.76 (1H, brs); 12.76 (1H, brs).

Example 5 4-hydroxy-3-(morpholinomethyl)quinoline-2-carboxylic acid hydrochloride Preparation starting from 4-hydroxyquinoline-2-carboxylic acid (A, 326 mg, 1.5 mmol), morpholine (175 mg, 2.0 mmol) and formaldehyde (22%, 410 mg, 3.0 mmol) according to example 1.

Yield: 443 mg (91%); M.p. 253-255° C. $^1$H NMR (D$_2$O); 3.26 (2H, t, J=8.4 Hz); 3.42 (2H, d, J=9.3 Hz); 3.75 (2H, t, J=8.8 Hz); 4.07 (2H, d, J=9.3 Hz); 4.54 (2H, s); 7.48 (1H, t, J=7.7 Hz); 7.66-7.79 (2H, m); 8.10 (1H, d, J=8.1 Hz)

Example 6 4-hydroxy-3-((piperidin-1-yl)methyl)quinoline-2-carboxylic acid hydrochloride Preparation starting from 4-hydroxyquinoline-2-carboxylic acid (A, 326 mg, 1.5 mmol), piperidine (170 mg, 2.0 mmol) and formaldehyde (22%, 410 mg, 3.0 mmol) according to example 1.

Yield: 353 mg (73%); M.p. 215-217° C. $^1$H NMR (D$_2$O); 1.38-1.81 (4H, m); 1.82-1.98 (2H, m); 2.98 (2H, t, J=8.8 Hz); 3.37 (2H, d, J=9.3 Hz); 4.38 (2H, s); 7.42 (1H, t, J=7.8 Hz); 7.57-7.79 (2H, m); 8.02 (1H, d, J=7.3 Hz).

Example 7 4-hydroxy-3-((4-methylpiperazin-1-yl)methyl)quinoline-2-carboxylic acid Preparation starting from 4-hydroxyquinoline-2-carboxylic acid (A, 326 mg, 1.5 mmol), 1-methyl-piperazine (200 mg, 2.0 mmol) and formaldehyde (22%, 410 mg, 3.0 mmol) according to example 1.

Yield: 352 mg (78%); M.p. 229-231° C. $^1$H NMR (DMSO); 2.32 (3H, s); 3.04-3.43 (8H, m); 4.34 (2H, s); 7.34 (1H, t, J=7.5 Hz); 7.65 (1H, t, J=7.4 Hz); 7.97 (1H, d, J=8.1 Hz); 8.09 (1H, d, J=7.8 Hz); 11.74 (1H, brs).

Example 8 4-hydroxy-3-(morpholinomethyl)-6-phenylquinoline-2-carboxylic acid Preparation starting from 4-hydroxy-6-phenylquinoline-2-carboxylic acid ethyl ester (A, 440 mg, 1.5 mmol), morpholine (175 mg, 2.0 mmol) and formaldehyde (22%, 410 mg, 3.0 mmol) according to example 1.

Yield: 421 mg (77%); M.p. 225-227° C. $^1$H NMR (DMSO); 2.67-2.93 (4H, m); 3.41-3.67 (4H, m); 4.19 (2H, s); 7.37.31-7.56 (2H, m); 7.63-7.79 (2H, m); 7.86-7.08 (2H, m); 8.25-8.43 (2H, m).

Example 9 7-chloro-4-hydroxy-3-(morpholinomethyl)quinoline-2-carboxylic acid Preparation starting from 4-hydroxy-7-chloroquinoline-2-carboxylic acid ethyl ester (A, 377 mg, 1.5 mmol), morpholine (175 mg, 2.0 mmol) and formaldehyde (22%, 410 mg, 3.0 mmol) according to example 1.

Yield: 402 mg (83%); M.p. 278-281° C. $^1$H NMR (DMSO); 2.97-3.35 (4H, m); 3.49-4.07 (4h, m); 4.38 (2H, s); 7.36 (1H, d, J=8.7 Hz); 8.08 (1H, d, J=7.5 Hz); 8.09 (1H, s); 11.85 (1H, brs); 12.53 (1H, brs).

Example 10 4-hydroxy-8-methyl-3-(morpholinomethyl)quinoline-2-carboxylic acid Preparation starting from 4-hydroxy-8-methylquinoline-2-carboxylic acid ethyl ester (A, 347 mg, 1.5 mmol), morpholine (175 mg, 2.0 mmol) and formaldehyde (22%, 410 mg, 3.0 mmol) according to example 1.

Yield: 390 mg (86%); M.p. 255-258° C. $^1$H NMR (DMSO); 2.52 (3H, s); 3.08-3.38 (4H, m); 3.58-4.01 (4H, m); 4.48 (2H, s); 7.27 (1H, t, J=7.8 Hz); 7.56 (1H, d, J=7.2 Hz); 7.96 (1H, d, J=8.1 Hz); 10.20 (1H, brs); 11.73 (1H, brs)

Example 11 3-((1,2,3,4-tetrahidroisoquinoline-2-yl)methyl)-4-hydroxyquinoline-2-carboxylic acid Preparation starting from 4-hydroxyquinoline-2-carboxylic acid ethyl ester (A, 326 mg, 1.5 mmol), 1,2,3,4-tetrahidroisoquinoline (266 mg, 2.0 mmol) and formaldehyde (22%, 410 mg, 3.0 mmol) according to example 1.

Yield: 406 mg (81%); M.p. 275-278° C. $^1$H NMR (DMSO); 3.01-3.16 (2H, m); 3.36-3.57 (2H, m); 4.32-4.46 (2H, m); 4.51 (2H, s); 7.17-7.32 (4H, m); 7.37 (1H, t, J=7.5 Hz); 7.69 (1H, t, J=7.6 Hz); 8.01 (1H, d, J=8.6 Hz); 8.13 (1H, d, J=8.0 Hz); 11.77 (1H, brs); 13.06 (1H, brs)

Example 12 3-((1,2,3,4-tetrahidro-6,7-dimethoxy-isoquinoline-2-yl)methyl)-4-hydroxy-quinoline-2-carboxylic acid Preparation starting from 4-hydroxyquinoline-2-carboxylic acid ethyl ester (A, 326 mg, 1.5 mmol), 6,7-dimethoxy-1,2,3,4-tetrahidro-isoquinoline (382 mg, 2.0 mmol) and formaldehyde (22%, 410 mg, 3.0 mmol) according to example 1.

Yield: 426 mg (72%); M.p. 248-250° C. $^1$H NMR (DMSO); 2.90-3.05 (2H, m); 3.34-3.45 (2H, m); 3.69 (3H, s); 3.74 (3H, s); 4.27 (2H, s); 4.50 (2H, s); 6.78 (1H, s); 6.82

(1H, s); 7.37 (1H, t, J=7.7 Hz); 7.68 (1H, t, J=7.4 Hz); 8.00 (1H, d, J=8.8 Hz); 8.13 (1H, d, J=7.8 Hz)

Example 13 3-((diethylamino)methyl)-N-(2-(dimethylamino)ethyl)-4-hydroxyquinoline-2-carboxamide Diethylamine (B, 146 mg, 2.0 mmol) and formaldehyde (22%, 410 mg, 3.0 mmol) were added to a suspension of the N-(2-(dimethyl amino)ethyl)-4-hydroxyquinoline-2-carboxamide (C, 390 mg, 1.5 mmol) in 30 ml 1,4-dioxane. The mixture was refluxed for 6 hours, the solvent was removed with evaporation, and the residue was crystallized from Et$_2$O.
Yield: 424 mg (82%); M.p.>350° C. $^1$H NMR (DMSO); 0.89-0.93 (6H, m); 2.09-2.12 (6H, m); 2.33 (2H, t, J=8.7 Hz); 2.42-2.49 (4H, m); 3.31 (2H, t, J=9.3 Hz); 3.70 (2H, s); 7.12 (1H, t, J=7.5 Hz); 7.36 (1H, t, J=7.6 Hz); 7.59 (1H, d, J=8.6 Hz); 7.97 (1H, d, J=8.0 Hz)

Example 14 N-(2-(dimethylamino)ethyl)-4-hydroxy-3-((pyrrolidin-1-yl)methyl)quino-line-2-carboxamide Preparation starting from N-(2-(dimethylamino)ethyl)-4-hydroxyquinoline-2-carboxamide (C, 390 mg, 1.5 mmol), pyrrolidine (B 142 mg, 2.0 mmol) and formaldehyde (22%, 410 mg, 3.0 mmol) according to example 13.
Yield: 385 mg (75%); M.p.>350° C. $^1$H NMR (DMSO); 1.61-1.87 (4H, m); 2.18 (6H, s); 2.42 (2H, t, J=6.3 Hz); 2.51-2.69 (4H, m); 3.41-3.52 (2H, m); 3.71 (2H, s) 7.30 (1H, t, J=7.1 Hz); 7.62 (1H, t, J=7.8 Hz); 7.86 (1H, d, J=8.1 Hz); 8.09 (1H, d, J=7.9 Hz); 11.30 (1H, brs); 11.63 (1H, brs

Example 15 N-(2-(dimethylamino)ethyl)-4-hydroxy-3-((piperidine-1-yl)methyl)quino-line-2-carboxyamide Preparation starting from N-(2-(dimethylamino)ethyl)-4-hydroxyquinoline-2-carboxamide (C, 390 mg, 1.5 mmol), piperidine (B 170 mg, 2.0 mmol) and formaldehyde (22%, 410 mg, 3.0 mmol) according to example 13.
Yield: 412 mg (77%); M.p.>350° C. 1.41-1.49 (6H, m); 2.20 (6H, s); 2.43-2.47 (4H, m); 3.42-3.45 (4H, m); 3.60 (2H, s) 7.26 (1H, t, J=7.3 Hz); 7.58 (1H, t, J=7 5 Hz); 7.79 (1H, d, J=8.7 Hz); 8.05 (1H, d, J=7.7 Hz)

Example 16 N-(2-(dimethylamino)ethyl)-4-hydroxy-3-(morpholinomethyl)quinoline-2--carboxamide Preparation starting from N-(2-(dimethylamino)ethyl)-4-hydroxyquinoline-2-carboxamide (C, 390 mg, 1.5 mmol), morpholine (B 170 mg, 2.0 mmol) and formaldehyde (22%, 410 mg, 3.0 mmol) according to example 13.
Yield: 425 mg (79%); M.p.>350° C. 2.19 (6H, s); 2.43-2.52 (6H, m); 3.42 (2H, t, J=7.3 Hz); 3.43-3.54 (4H, m); 3.64 (2H, s) 7.17 (1H, t, J=7.3 Hz); 7.48 (1H, t, J=7.7 Hz); 7.68 (1H, d, J=8.3 Hz); 8.06 (1H, d, J=8.1 Hz)

Example 17 3-((diethylamino)methyl)-4-hydroxy-N-(2-(pyrrolidin-1-yl)ethyl)quinoline-2-carboxamide Preparation starting from 4-hydroxy-N-(2-(pyrrolidin-1-yl)ethyl)quinoline-2-carboxamide (D, 428 mg, 1.5 mmol), diethylamine (B, 146 mg, 2.0 mmol) and formaldehyde (22%, 410 mg, 3.0 mmol) according to example 13.
Yield: 422 mg (76%); M.p.>350° C. 1.01-1.21 (10H, m); 1.75-2.11 (6H, m); 2.53-3.21 (4H, m); 3.41-3.52 (2H, m); 4.12 (2H, s) 7.30 (1H, t, J=7.1 Hz); 7.62 (1H, t, J=7.8 Hz); 7.86 (1H, d, J=8.1 Hz); 8.09 (1H, d, J=7.9 Hz)

Example 18 4-hydroxy-N-(2-(pyrrolidin-1-yl)ethyl)-3-((pyrrolidin-1-yl)methyl)quino-line-2-carboxamide Preparation starting from 4-hydroxy-N-(2-(pyrrolidin-1-yl)ethyl)quinoline-2-carboxamide (D, 428 mg, 1.5 mmol), pyrrolidine (B, 170 mg, 2.0 mmol) and formaldehyde (22%, 410 mg, 3.0 mmol) according to example 13.
Yield: 392 mg (71%); O.p.>350° C. 1.53-1.68 (8H, m); 2.53-2.68 (6H, m); 3.38-3.46 (6H, m); 3.81 (2H, s) 7.15 (1H, t, J=7.3 Hz); 7.46 (1H, t, J=7.5 Hz); 7.66 (1H, d, J=8.3 Hz); 8.06 (1H, d, J=7.8 Hz); 10.07 (1H, brs)

Example 19 4-hydroxy-3-((piperidin-1-il)methyl)-N-(2-(pyrrolidin-1-yl)ethyl)quinoline-2-carboxamide Preparation starting from 4-hydroxy-N-(2-(pyrrolidin-1-yl)ethyl)quinoline-2-carboxamide (D, 428 mg, 1.5 mmol), piperidine (B, 170 mg, 2.0 mmol) and formaldehyde (22%, 410 mg, 3.0 mmol) according to example 13.
Yield: 470 mg (82%); M.p.>350° C. 1.34-1.51 (6H, m); 1.68-1.70 (4H, m); 2.49-2.51 (8H, m); 2.63 (2H, t, J=8.1 Hz); 3.48 (2H, t, J=8.7 Hz); 3.61 (2H, s) 7.31 (1H, t, J=7.3 Hz); 7.63 (1H, t, J=7.7 Hz); 7.86 (1H, d, J=8.0 Hz); 8.08 (1H, d, J=7.8 Hz)

Example 20 4-hydroxy-3-(morpholinomethyl)-N-(2-(pyrrolidin-1-il)ethyl)quinoline-2--carboxyamide Preparation starting from 4-hydroxy-N-(2-(pyrrolidin-1-yl)ethyl)quinoline-2-carboxamide (D, 428 mg, 1.5 mmol), morpholine (B, 170 mg, 2.0 mmol) and formaldehyde (22%, 410 mg, 3.0 mmol) according to example 13.
Yield: 438 mg (76%); M.p.>350° C. $^1$H NMR (DMSO); 1.34-1.57 (8H, m); 1.62-1.75 (4H, m); 2.37-2.52 (4H, m); 2.64 (2H, t, J=6.2 Hz); 3.46-3.53 (2H, m); 3.57 (2H, s); 7.33 (1H, t, J=7.8 Hz); 7.65 (1H, t, J=7.9 Hz); 7.88 (1H, d, J=8.2 Hz); 8.09 (1H, d, J=8.0 Hz); 11.32 (1H, brs); 11.69 (1H, brs).

Example 21 4-hydroxy-3-(morpholinomethyl)quinoline-2-carboxylic acid methyl ester In a 50 ml round bottom flask 576 mg (2.0 mmol) 4-hydroxy-3-(morpholinomethyl)quinoline-2-carboxylic acid (5) was dissolved in 20 ml MeOH. The mixture was agitated with 1 ml Et$_2$O solution of CH$_2$N$_2$ at room temperature for 5 hours. Following the removal of the solvent the residue was crystallized from n-hexane:EtOAc.
Yield: 405 mg (67%); M.p. 122-123° C. $^1$H NMR (DMSO); 2.97-3.07 (2H, m); 3.19-3.25 (4H, m); 3.31 (2H, s); 3.35-3.42 (2H, m); 3.98 (3H, s); 7.35 (1H, t, J=7.7 Hz); 7.69 (1H, t, J=8.1 Hz); 7.78 (1H, d, J=7.8 Hz); 8.10 (1H, d, J=8.7 Hz)

Example 22 4-hydroxy-3-(morpholinomethyl)quino-line-2-carboxamide 4-hydroxyquinoline-2-carboxylic acid amide 22A 4-hydroxyquinoline-2-carboxylic acid ethyl ester (A, 652 mg, 3.0 mmol) and NH$_3$/MeOH (20%, 5 ml) were placed in a pressure-resistant vessel of 10 ml. The mixture was kept at 100° C. for 30 minutes with a CEM Discover SP microwave oven reactor. Following the removal of the solvent the residue was crystallized from 10 ml Et$_2$O.

Yield: 406 mg (72%); M.p. 309-311° C. $^1$H NMR (DMSO); 6.78 (1H, s); 7.34 (1H, t, J=7.0 Hz); 7.67 (1H, t, J=7.7 Hz); 7.95 (1H, d, J=8.3 Hz); 7.98-8.10 (2H, m); 8.43 (1H, s); 11.72 brs A Reaction Route:

Preparation starting from 4-hydroxyquinoline-2-carboxamide (22A, 150 mg, 0.8 mmol), morpholine (88 mg, 1.0 mmol) and formaldehyde (22%, 410 mg, 3.0 mmol) according to example 1.

B Reaction Route:

Preparation starting from 4-hydroxy-3-(morpholinomethyl)-quinoline-2-carboxylic acid methyl ester (12, 150 mg, 0.5 mmol) and NH$_3$/MeOH (20%, 5 ml) according to example 22A.

Yield: 126 mg (88%). M.p. 143-146° C. $^1$H NMR (DMSO); 2.45 (4H, s); 3.52 (4H, s); 3.59 (2H, s); 7.33 (1H, t, J=7.7 Hz); 7.66 (1H, t, J=7.3 Hz); 7.86 (1H, d, J=7.9 Hz); 8.08 (1H, d, J=8.2 Hz); 8.20 (1H, brs); 10.07 (1H, brs)

Example 23 N-benzyl-4-hydroxy-3-(morpholinomethyl)quinoline-2-carboxamide

N-benzyl-4-hydroxyquinoline-2-carboxamide

Preparation starting from 4-hydroxyquinoline-2-carboxylic acid ethyl ester (A, 652 mg, 3.0 mmol) and benzylamine (535 mg, 5.0 mmol) according to example 22.

Yield: 625 mg (75%); M.p. 297-300° C. $^1$H NMR (DMSO); 4.52 (2H, d, J=6.3 Hz); 6.79 (1H, s); 7.22-7.43 (6h, m); 7.68 (1H, t, J=7.4 Hz); 7.93 (1H, d, J=8.1 Hz); 8.08 (1H, t, J=7.9 Hz); 9.53 (1H, brs); 11.82 (1H, brs)

A Reaction Route:

Preparation starting from N-benzyl-4-hydroxyquinoline-2-carboxamide (23A1, 223 mg, 0.8 mmol), morpholine (88 mg, 1.0 mmol) and formaldehyde (22%, 273 mg, 2.0 mmol) according to example 1.

B Reaction Route:

Preparation starting from 4-hydroxy-3-(morpholinomethyl)quinoline-2-carboxylic acid methyl ester (12, 150 mg, 0.5 mmol) and benzylamine (214 mg, 2.0 mmol) according to example 22.

Yield A: 214 mg (71%); Yield B: 175 mg (93%); M.p. 198-202° C. $^1$H NMR (DMSO); 2.24 (4H, s); 3.18 (4H, s); 3.55 (2H, s); 4.59 (2H, d, J=5.4 Hz); 7.28-7.47 (6H, m); 7.67 (1H, t, J=7.9 Hz); 7.90 (1H, d, J=8.7 Hz); 8.08 (1H, d, J=7.8 Hz); 11.27 (1H, brs); 11.85 (1h, brs)

Biological Examples

Example 24 Testing the Passage of the C-3 Substituted Kynurenic Acid Derivatives of the Invention on the Culture Model of the Blood-Brain Barrier, Compared to the Derivatives not Substituted in the C-3 Position The blood-brain barrier model prepared by the co-cultivation of three cell types (primary rat brain endothelial cells, primary glia and brain microvascular pericyte cells) was used for the permeability experiments (Nakagawa S, Deli M A, Kawaguchi H, Shimizudani T, Shimono T, Kittel A, Tanaka K, Niwa M. Anew blood-brain barrier model using primary rat brain endothelial cells, pericytes and astrocytes. Neurochem Int. 2009 March-April; 54(3-4):253-63. doi: 10.1016/j.neuint.2008.12.002.; Veszelka S, Tóth A E, Walter F R, Datki Z, Mózes E, Fülöp L, Bozsó Z, Hellinger E, Vastag M, Orsolits B, Környei Z, Penke B, Deli M A. Docosahexaenoic acid reduces amyloid-β induced toxicity in cells of the neurovascular unit. J Alzheimers Dis. 2013; 36(3):487-501.).

Passage of the compounds of the invention was tested in two directions AB ("from blood to brain") and BA ("from brain to blood"), in 10 μM concentration.

The permeability experiment took 60 minutes, with sampling at 30 and 60 minutes from the acceptor compartment.

The concentrations of the active substances passed through the endothelial cell layer were determined with mass spectrometry. By using the measured concentrations and the known data (volume, starting concentration) the clearance (μl) values, or from the clearance and volume data, by taking the surface and the time into consideration, the so-called permeability coefficients ($p_{app}$, apparent permeability coefficient; measurement unit $10^{-6}$ cm/s) were calculated, which provide the permeation rates of the compounds.

The compounds tested:

| Example | Structure | Name |
|---|---|---|
| 24/2 comparative example [Curr. Med. Chem., 16, 4828-42 (2009)] | (structure: 4-hydroxyquinoline-2-carboxamide with N-(2-(dimethylamino)ethyl) side chain, HCl salt) | N-(2-(dimethylamino)ethyl)-4-hydroxyquinoline-2-carboxamide |
| 24/1 comparative example [Curr. Med. Chem., 16, 4828-42 (2009)] | (structure: 4-hydroxyquinoline-2-carboxamide with N-(2-(pyrrolidin-1-yl)ethyl) side chain, HCl salt) | 4-hydroxy-N-(2-(pyrrolidin-1-yl)ethyl)quinoline-2-carboxamide |

-continued

| Example | Structure | Name |
|---|---|---|
| Example 5 | 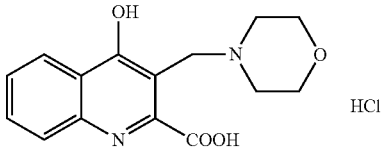 [SMILES: O=C(O)c1nc2ccccc2c(O)c1CN1CCOCC1 ; Cl] | 4-hydroxy-3-(morpholinomethyl)quinoline-2-carboxylic acid hydrochloride |
| Example 16 | 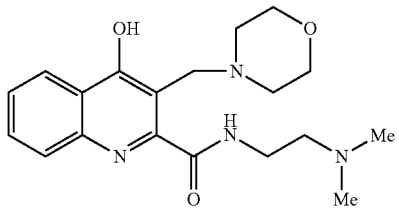 [SMILES: CN(C)CCNC(=O)c1nc2ccccc2c(O)c1CN1CCOCC1] | N-(2-(dimethylamino)ethyl)-4-hydroxy-3-(morpholinomethyl)quinoline-2-carboxamide |
| Example 20 | 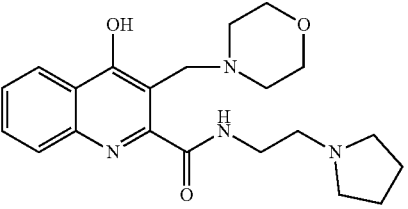 [SMILES: O=C(NCCN1CCCC1)c1nc2ccccc2c(O)c1CN1CCOCC1] | 4-hydroxy-3-(morpholinomethyl)-N-(2-(pyrrolidin-1-il)ethyl)quinoline-2-carboxamide |

Evaluation of the In Vitro Transport Results

Figure 2:
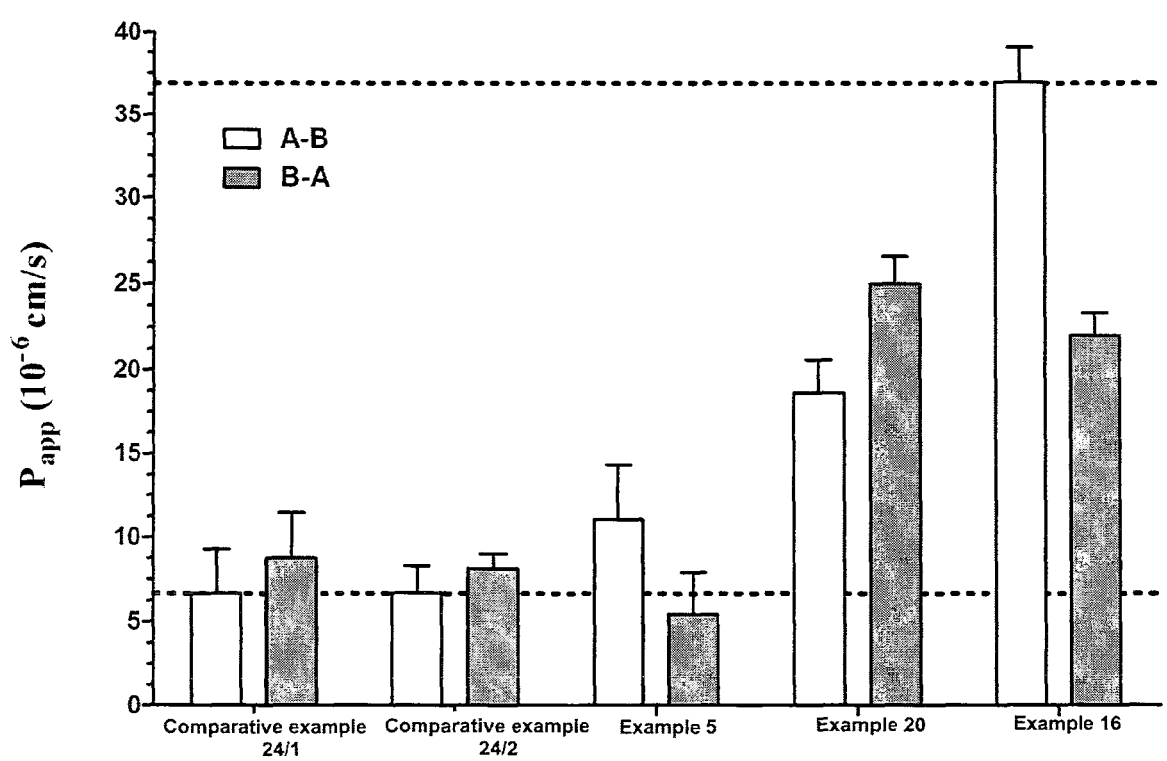
FIG. 2 The permeability investigation of compounds of Examples 24/1, 24/2 and 5, 16 and 20 on blood-brain barrier model (n=6).
Figure 3:
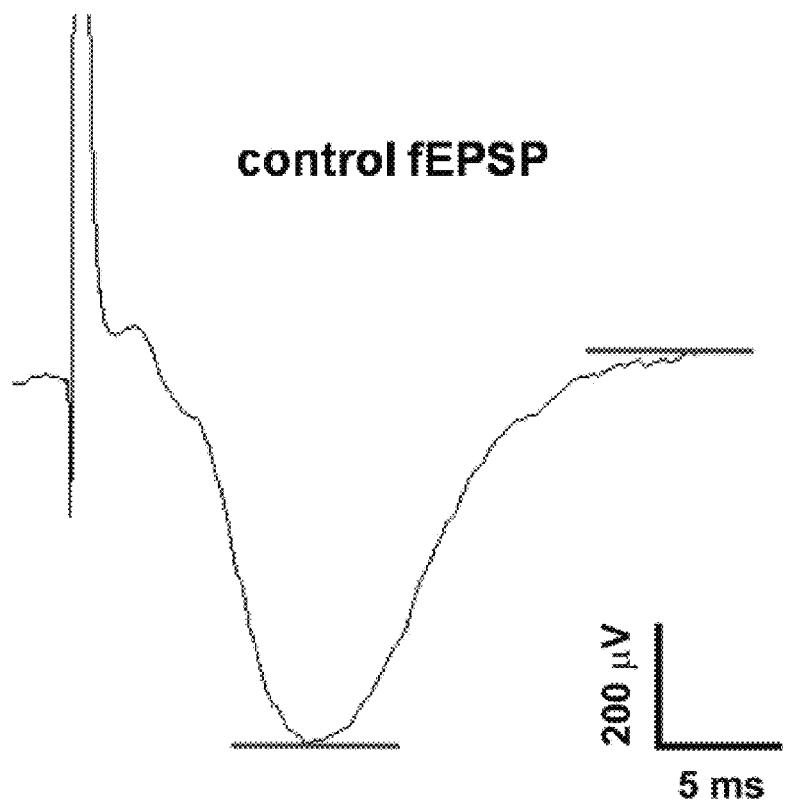
FIG. 3 A control graph showing stimulating postsynaptic field potentials (fEPSP).
Figure 1:
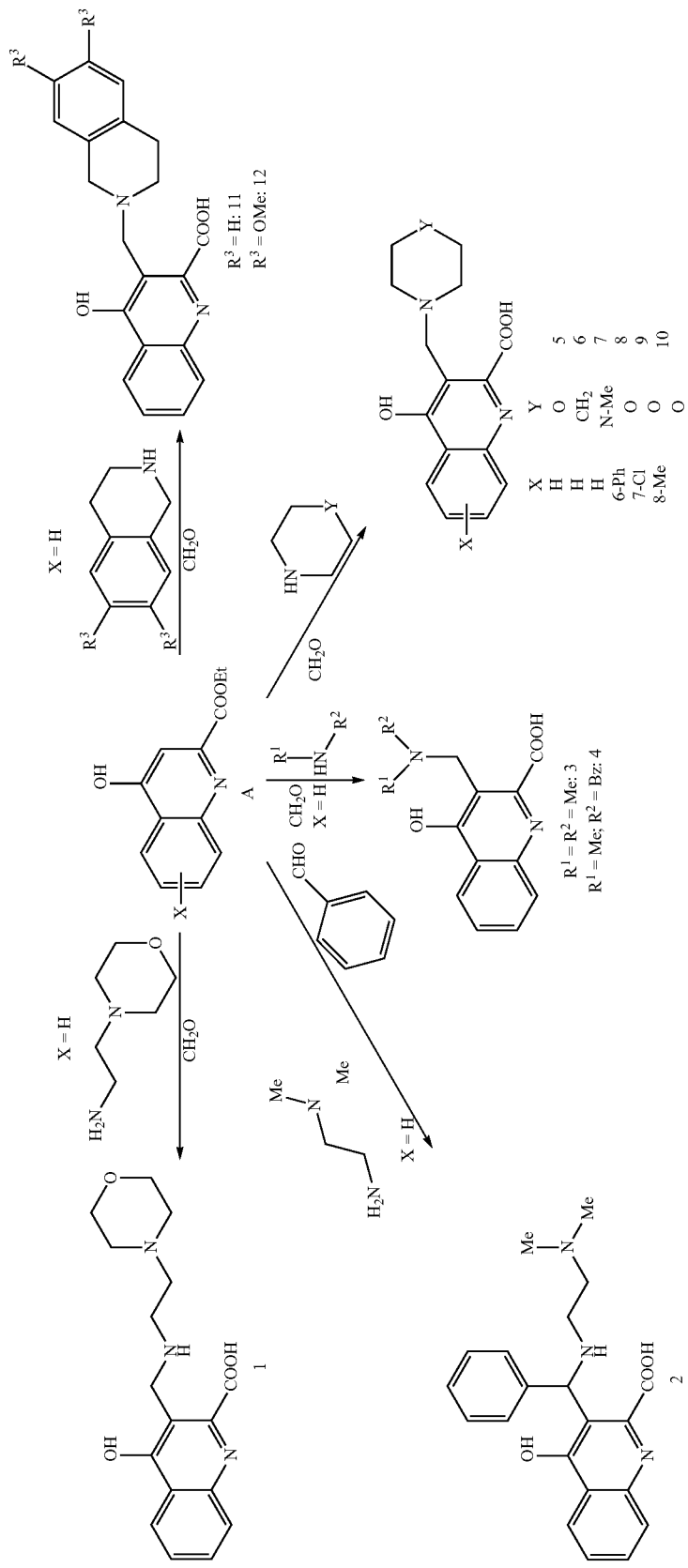

The two-way passage of each test substance could be measured in the blood-brain barrier model (FIGS. 1 and 2). It is known from the literature (Curr. Med. Chem., 16, 4828-42) that the kynurenic acid derivatives unsubstituted in position 3 (comparative example 24/1 and comparative example 24/2) showed similar low passage in both directions. Passage of the compound of Example 5 is doubled compared to the previous comparative compounds. In case of the compound of Example 20 the passage value is already triple, compared to 24/1, 24/2 comparative amides with no substitution in the C-3 position. The highest passage through the blood-brain barrier was presented by the compound of Example 16. In this case the passage was six times higher than that of the 24/1 and 24/2 comparative compounds (FIG. 2).

Based on the following results it can be stated that the C-3 substituent promotes brain penetration, i.e. on the basis of the $P_{app}$ values of AB direction measured for the compounds having a substituent in the position C-3 the good nervous system effect can be supposed (Table 2).

In the case of the compounds of Example 24/1, 24/2 and 20 similar passage value was obtained in both directions in the blood-brain barrier model, the efflux ratio is around 1, supposing a passive permeability. In case of compounds with the medium permeability (compound according to Example 5) and with the high permeability (compound according to Example 16) the permeability in AB direction is significantly higher (the efflux ratio is around 0.5), which may even indicate an active transport towards the brain through the blood-brain barrier.

TABLE 2

Summary of the $P_{app}$ values of the compounds of Examples 24/1, 24/2, 5, 20 and 16
Efflux ratio: $P_{app}BA/P_{app}AB$

| | $P_{app}$ A-B ($10^{-6}$ cm/s) | | | | $P_{app}$ B-A ($10^{-6}$ cm/s) | | | | Efflux ratio |
|---|---|---|---|---|---|---|---|---|---|
| | 30' | 60' | Average | ±SD | 30' | 60' | Average | ±SD | |
| comparative 24/1 | 7.4 | 5.8 | 5.7 | 1.6 | 4.2 | 9.2 | 8.8 | 2.7 | 1.5 |
| | 5.4 | 7.2 | | | 8.3 | 12.2 | | | |
| | 4.5 | 3.9 | | | 8.1 | 10.5 | | | |
| comparative 24/2 | 4.2 | 6.0 | 6.7 | 1.6 | 7.6 | 9.7 | 8.1 | 0.9 | 1.2 |
| | 8.3 | 8.4 | | | 7.9 | 7.9 | | | |
| | 6.4 | 6.7 | | | 7.2 | 8.5 | | | |
| Example 5 | 7.4 | 12.4 | 11.0 | 3.3 | 2.5 | 7.6 | 5.4 | 2.5 | 0.5 |
| | 8.9 | 15.4 | | | 4.0 | 7.8 | | | |
| | 8.2 | 13.9 | | | 3.2 | 7.5 | | | |
| Example 20 | 16.4 | 16.9 | 18.6 | 2.0 | 22.3 | 24.9 | 25.0 | 25.0 | 1.3 |
| | 20.1 | 21.5 | | | 24.3 | 26.7 | | | |
| | 17.9 | 18.8 | | | 25.1 | 26.6 | | | |
| Example 16 | 32.7 | 37.8 | 36.9 | 2.1 | 20.1 | 21.7 | 22.0 | 1.3 | 0.6 |
| | 37.2 | 37.4 | | | 21.8 | 23.2 | | | |
| | 38.0 | 38.6 | | | 21.3 | 23.8 | | | |

Example 25. In Vitro Electrophysiological Testing of the Compounds of Invention Animals Used in the Experiments In the course of our experiments young adult (200-250 g) male Wistar rats were used. Until the start of the experiments the animals were housed in the animal house of the Department of Physiology, Anatomy and Neuroscience, University of Szeged, in standard plastic cages, where 12-12 hours light-dark cycles, standard 23° C. temperature and free access to water and food were provided. In the course of the experiments we aimed at using a minimum number of animals and to cause them the smallest degree of suffering. In each case the principles relating to the care of laboratory animals, the animal care related protocol approved by the Hungarian Health Committee (1998), and the Decree of the Council of the European Communities of 22 Sep. 2010 (2010/63/EU) were followed.

The Methodology of the Hippocampal Brain Slice Preparation

The animals received Isoflurane (3% and then 1%) inhalation anaesthesia for the electrophysiological measurements. After ensuring that the animals were in a deep sleep phase (the paw withdrawal reflex occurring for squeezing stopped), they were decapitated. By incising the head skin and the underlying connective tissue the skull was exposed. Then incisions were made in longitudinal direction along the sagittal suture as well as in transversal direction along the suture coronalis, furthermore caudally therefrom in the right and left direction. After the opening the bregma coronalis incisions were made behind the bulbi and in front of the cerebellum, allowing the removal of the approx. 3 mm thick brain region, containing the hippocampus. From the middle part of the hippocampus 350 μm thick slices were prepared with vibratome (Leica VT1200S, Germany). The cutting was performed in artificial cerebrospinal fluid (aCSF), whose temperature was 4° C. *maximum*. The aCSF was composed of: 130 mM NaCl, 3.5 mM KCl, 1 mM $NaH_2PO_4$, 24 mM $NaHCO_3$, 1 mM $CaC_2$, 3 mM $MgSO_4$ and 10 mM D-glucose (Sigma, Germany). The cut slices were placed in recording aCSF of room temperature, whose composition differed only in the 3 mM $CaCl_2$) and 1.5 $MgSO_4$ concentrations from the one used for cutting. Both the cutting and the recording aCSF were oxygenated with carbogen (95% $O_2$, 5% $CO_2$), for providing the suitable and uninterrupted $O_2$ supply. After the preparation of all the hippocampal slices the recording aCSF in the slice holder container was warmed to 34-35° C., and the brain slices were left to recover for one hour under these conditions in order to assure the proceeding of the regeneration processes started against the damages caused in the course of the slice-preparation. Then the cooling of the liquid was started, and the brain slices were kept at constant 16-18° C. until the starting the experiments. The slices were placed in the recording chamber of Haas type, where at 34° C., in humid environment, with the perfusion of the recording aCSF they were rested for approx. half an hour until starting the experiment. The flow rate of the perfusion aCSF in the chamber was about 2 ml/min.

In Vitro Electrophysiology

For the electrophysiological recordings a concentric stainless steel electrode (Neuron elektród kft; Budapest, Hungary) was placed in the stratum radiatum layer between the CA3-CA1 regions of the hippocampus, wherein the stimulation was performed with constant current intensity, with 0.2 ms pulses of 0.033 Hz frequency. By positioning the recording electrodes of 2-3 MΩ filled with aCSF in orthodrom position from the previously mentioned region, stimulating postsynaptic field potentials (fEPSP) were conducted from the stratum radiatum layer of the CA1 region, and their amplitudes were monitored. See FIG. 3.

Submaximal stimulation was used, i.e. about 70-80% of the intensity of the smallest pulse causing the fEPSP of maximum amplitude was used. Recording of the fEPSP was carried out with an analogue-digital converter, on a computer provided with a recording program. (Experimetria; AIF-03). The results were evaluated with the OriginPro 8 (OriginLab Corporation, Northampton, Mass., USA) software.

The slices were rested with the parameters mentioned above by stimulating them for minimum 30 minutes, in order to let the fEPSP-s to stabilize. As soon as this was done, a control phase of 10 minutes was recorded, which was followed by washing in of the derivative of the invention for 30 minutes. Then an additional 30 minutes washing off phase was applied, wherein the pure aCSF was perfunded for the slices. See FIG. 4.

Before the measurements stock solutions of 20M were prepared from the compounds of the invention. Depending on the compound, the solvent used was 1 N HCl or 1 N NaOH. By diluting the stock solution with previously oxygenated aCSF a 200 μM solution was prepared, and in the washing in phase it was perfunded to the slices. The pH of the solution was checked in each case, and when it was necessary it was adjusted to physiological value (pH=7.4) by titration.

Results

The compound of Example 20 (N=8) significantly reduced the amplitudes of the fEPSP-s. By normalizing to the averages of the amplitudes measured in the control phase said amplitude was 58.14±10.16% in the last 10 minutes of washing in. The effect was reversible, because in the washing off phase the fEPSP amplitudes started to grow, and for the last 10 minutes of the recording took up values close to the control section (107.14±17.99%).

The compound of Example 17 (N=5) significantly increased the amplitudes of the fEPSP-s, which in the last 10 minutes of washing off had a value of 124.66±10.43%. This was reversible with the washing off, in this phase the fEPSP-s showed continuous decrease, and by the end of the recording were close to the control level (110.73±7.63%).

The results are demonstrated in the following Table 3:

TABLE 3

| Example | Minutes 31-40 of recording (washing in phase) | Minutes 61-70 of recording (washing off phase) |
|---|---|---|
| Example 20 | 58.14 ± 10.16% | 107.14 ± 17.99% |
| Example 17 | 124.66 ± 10.43% | 110.73 ± 7.63% |

Explanation of the Results

For our experiments the 200 μM test concentration was selected on the basis of our preliminary experimental results obtained with kynurenic acid, because with this concentration well reproducible, significant differences were experienced in each measurement. In the last 10 minutes of the washing in phase the kynurenic acid resulted in amplitude decrease of 53.86±6.09%. The effect of the compound of Example 20 was the same as that of the kynurenic acid. Probably the inhibitory effect exerted through the NMDA receptors is in the background of the phenomenon. In addition, it is important to highlight the more advantageous characteristics of this new molecule (for example better solubility, physiologic pH easier to achieve), compared to the previously synthesized analogues, or to other analogues having similar effect. The synaptic transmission inhibitory effect of the compound of example 20 may provide a protective effect for the nerve tissue in diseased conditions involving NMDA receptor overactivity.

In the test concentration the compound of Example 17 caused an increase in the synaptic transmission, which probably prevailed through the α7nACh receptors. The α7nACh receptors play a significant role in the cognitive functions: they play a critical role in the development of learning and memory functions, or in the general synaptic plasticity. Their effect is exerted through the regulation of the stimulatory neurotransmitter (glutamate) release. If the compound of Example 17 functions as agonist of the α7nACh receptor, it explains the increase in amplitude of the fEPSP-s. The activation of said receptors promotes the development of the long-term potentiation in the hippocampus (by increasing the glutamatergic tone), which ultimately enhances both the cognition abilities and the synaptic plasticity, this way the compounds of the invention may be used for retarding the progress of conditions and diseases associated with the decline in cognitive abilities.

Example 26

In Vivo Testing the Compounds of the Invention

The experiments performed with hippocampal brain slice preparations are considered to be a generally accepted methodology in the field of neuroprotection research. Examination of the different pharmacons doesn't take place only in the given in vitro disease models, but before that, of course, in control conditions too (Picconi et al., 2006; Nistico et al., 2008). In this case monitoring of the possible synaptic transmission changes occurring as a consequence of washing in of the active ingredient is happening. If the given pharmacon has neuroactive effect, it manifests even in the change of the conducted fEPSP parameters (for example their amplitude, slope). In our experiments a pre-screening was conducted with the in vitro tests for the compounds of the invention, and then they were used in the in vivo animal tests. In our in vivo measurements the derivatives of Example 20 and Example 17 were examined in a combined cortical spreading depolarization (CSD) model (induced by nitroglycerine (NTG)+KCl). Before the surgical preparation was performed on the animals anaesthesia was used with isoflurane (3%) (Florane, Harvard Apparatus Isoflurane Vaporizer), which was followed by the intraperitoneal urethane injection (1.5 g/kg body weight, 20%).The proper depth of anaesthesia was proven by the lack of the cornea reflex and the lack of response given to the mild pain stimuli of the hind limb. In the first step of the surgical preparation tracheal cannulation was performed for ensuring proper breathing even in case if oedema develops as a consequence of the surgery. Then the heads of the animals were fixed in a stereotactic holder, and then the scalp was removed. Following the appropriate preparation the skull was opened in 4 locations with a dental drill for the electrophysiological measurements, in the following positions relative to Bregma (+mm; −2 mm), (−2 mm; −2 mm); (−5 mm; −2 mm), (−2 mm; +2 mm). During the experiment the open brain areas were kept constantly wept by the fine dosing of the ACSF (artificial cerebrospinal fluid). Upon completion of the surgical preparation the measurements were carried out with a recording equipment provided with a Faraday cage, and throughout the duration of the measurement the constant temperature of the animals (37° C.) was ensured with heating pad (Supertech Kft.). Electrocorticogram (ECoG) was conducted from 2 points, from 1 point DC-ECoG was conducted, and point 4 was the location of inducing the cortical spreading depolarization (CSD) (this was performed by the introduction of 1 M KCl solution to the surface of the brain). In the course of the experiments the different parameters of the CSD waves (number, propagation speed, propagation rate, etc.) were investigated, and were compared in the different experimental groups (in the control, CSD, NTG-CSD, sumatriptane (SUMA), derivatives of Examples 17 and 20 experimental groups). Our results demonstrate (Table 4) that the compounds of Example 20 and 17 reduced the cortical hyperexcitability induced by nitroglycerine used in the CSD model. In respect of this activity they showed better results than the SUMA, which is an active ingredient widely used in the clinical practice for the acute treatment of migraine. This way the SUMA is a good reference molecule for the validation of the antimigraine screening models, or for the comparison with new active ingredients.

TABLE 4

| Test groups | Propagation ratio of the CSD waves |
| --- | --- |
| control | 0.80193 +− 0.13628 |
| NTG | 1.02492 +− 0.09056 |
| NTG + SUMA | 1.02763 +− 0.14235 |
| Example 20 | 0.78671 +− 0.19238 |
| Example 17 | 0.76543 +− 0.10382 |

The above hyperexcitability reduction demonstrates well the neuroprotective effect of the compounds of the inventions.

REFERENCES

Picconi B, Barone I, Pisani A, Nicolai R, Benatti P, Bernardi G, Calvani M, Calabresi P (2006) Acetyl-L-carnitine protects striatal neurons against in vitro ischemia: the role of endogenous acetylcholine. Neuropharmacology 50:917-923.

Nistico R, Piccirilli S, Cucchiaroni M L, Armogida M, Guatteo E, Giampa C, Fusco F R, Bernardi G, Nistico G, Mercuri N B (2008) Neuroprotective effect of hydrogen peroxide on an in vitro model of brain ischaemia. British journal of pharmacology 153:1022-1029.

The invention claimed is:

1. A compound of formula (I)

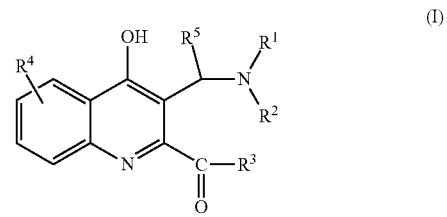

wherein
R$^1$ and R$^2$ are C$_{1-7}$alkyl; or
R$^1$ and R$^2$ with the nitrogen atom to which they are attached form a saturated 5-6 membered, optionally benzofused heterocyclic ring;
R$^3$ is —NH—(CH$_2$)$_2$—NR$^8$R$^9$;
R$^4$ is H, C$_{1-7}$alkyl-, C$_{6-10}$ aryl group, or halogen;
R$^5$ is H or C$_{6-10}$aryl group;
and
R$^8$ and R$^9$ are each independently methyl or ethyl;
or a stereoisomer, tautomer, and pharmaceutically acceptable salt thereof.

2. A compound selected from the group consisting of:
3-((2-morpholinoethylamino)methyl)-4-hydroxyquinoline-2-carboxylic acid;
3-((2-(dimethyl amino)ethyl amino)(phenyl)methyl)-4-hydroxyquinoline-2-carboxylic acid;
3-((dimethyl amino)methyl)-4-hydroxyquinoline-2-carboxylic acid;
3-((benzyl methyl amino)methyl)-4-hydroxyquinoline-2-carboxylic acid;
4-hydroxy-3-(morpholinomethyl)quinoline-2-carboxylic acid;

4-hydroxy-3-((piperidin-1-yl)methyl)quinoline-2-carboxylic acid;
4-hydroxy-3-((4-methylpiperazin-1-yl)methyl)quinoline-2-carboxylic acid;
4-hydroxy-3-(morpholinomethyl)-6-phenylquinoline-2-carboxylic acid;
7-chloro-4-hydroxy-3-(morpholinomethyl)quinoline-2-carboxylic acid;
4-hydroxy-8-methyl-3-(morpholinomethyl)quinoline-2-carboxylic acid;
3-((1,2,3,4-tetrahydroisoquinoline-2-yl)methyl)-4-hydroxyquinoline-2-carboxylic acid;
3-((1,2,3,4-tetrahydro-6,7-dimethoxyisoquinoline-2-yl)methyl)-4-hydroxyquinoline-2-carboxylic acid;
3-((diethyl amino)methyl)-N-(2-(dimethyl amino)ethyl)-4-hydroxyquinoline-2-carboxylic acid amide;
N-(2-(dimethyl amino)ethyl)-4-hydroxy-3-((pyrrolidin-1-yl)methyl)quinoline-2-carboxylic acid amide;
N-(2-(dimethyl amino)ethyl)-4-hydroxy-3-((piperidine-1-yl)methyl)quinoline-2-carboxylic acid amide;
N-(2-(dimethyl amino)ethyl)-4-hydroxy-3-(morpholinomethyl)quinoline-2-carboxylic acid amide;
3-((diethyl amino)methyl)-4-hydroxy-N-(2-(pyrrolidin-1-yl)ethyl)quinoline-2-carboxylic acid amide;
4-hydroxy-N-(2-(pyrrolidin-1-yl)ethyl)-3-((pyrrolidin-1-yl)methyl)quinoline-2-carboxylic acid amide;
4-hydroxy-3-((piperidin-1-yl)methyl)-N-(2-(pyrrolidin-1-yl)ethyl)quinoline-2-carboxylic acid amide;
4-hydroxy-3-(morpholinomethyl)-N-(2-(pyrrolidin-1-yl)ethyl)quinoline-2-carboxylic acid amide;
4-hydroxy-3-(morpholinomethyl)quinoline-2-carboxylic acid methyl ester;
4-hydroxy-3-(morpholinomethyl)quinoline-2-carboxylic acid amide;
N-benzyl-4-hydroxy-3-(morpholinomethyl)quinoline-2-carboxylic acid amide;
or a stereoisomer, tautomer, and pharmaceutically acceptable salt thereof.

3. The compound according to claim 2, selected from the group consisting of:
4-hydroxy-3-(morpholinomethyl)quinoline-2-carboxylic acid;
3-((1,2,3,4-tetrahydroisoquinoline-2-yl)methyl)-4-hydroxyquinoline-2-carboxylic acid;
3-((1,2,3,4-tetrahydro-6,7-dimethoxyisoquinoline-2-yl)methyl)-4-hydroxyquinoline-2-carboxylic acid;
N-(2-(dimethyl amino)ethyl)-4-hydroxy-3-(morpholinomethyl)quinoline-2-carboxylic acid amide;
3-((diethyl amino)methyl)-4-hydroxy-N-(2-(pyrrolidin-1-yl)ethyl)quinoline-2-carboxylic acid amide;
4-hydroxy-N-(2-(pyrrolidin-1-yl)ethyl)-3-((pyrrolidin-1-yl)methyl)quinoline-2-carboxylic acid amide;
4-hydroxy-3-(morpholinomethyl)-N-(2-(pyrrolidin-1-yl)ethyl)quinoline-2-carboxylic acid amide;
or a stereoisomer, tautomer, and pharmaceutically acceptable salt thereof.

4. A pharmaceutical preparation comprising a compound according to claim 1, or a stereoisomer, tautomer, and pharmaceutically acceptable salt thereof, and one or more pharmaceutically acceptable carriers and/or vehicles.

5. A pharmaceutical preparation comprising a compound according to claim 2, or a stereoisomer, tautomer, and pharmaceutically acceptable salt thereof, and one or more pharmaceutically acceptable carriers and/or vehicles.

6. A method for providing a neuroprotective effect in a patient in need thereof, comprising administering to the patient a therapeutically effective amount of a compound according to claim 1, or a stereoisomer, tautomer, and pharmaceutically acceptable salt thereof.

7. A method for providing a neuroprotective effect in a patient in need thereof, comprising administering to the patient a therapeutically effective amount of a compound of claim 2, or a stereoisomer, tautomer, and pharmaceutically acceptable salt thereof.

8. The compound according to claim 1, wherein
$R^1$ and $R^2$ are each independently methyl, ethyl, or benzyl;
or a stereoisomer, tautomer, and pharmaceutically acceptable salt thereof.

9. The compound according to claim 1, wherein
$R^1$ and $R^2$ with the nitrogen atom to which they are attached form morpholinyl, pyrrolidinyl, piperidinyl, or piperazinyl;
or a stereoisomer, tautomer, and pharmaceutically acceptable salt thereof.

10. The compound according to claim 1, wherein
$R^1$ and $R^2$ with the nitrogen atom to which they are attached form tetrahydroisoquinolinyl;
or a stereoisomer, tautomer, and pharmaceutically acceptable salt thereof.

11. The compound according to claim 1, wherein
$R^8$ and $R^9$ are both methyl;
or a stereoisomer, tautomer, and pharmaceutically acceptable salt thereof.

12. The compound according to claim 3, wherein the compound is 4-hydroxy-3-(morpholinomethyl)quinoline-2-carboxylic acid.

13. The compound according to claim 3, wherein the compound is 3-((1,2,3,4-tetrahydroisoquinoline-2-yl)methyl)-4-hydroxyquinoline-2-carboxylic acid.

14. The compound according to claim 3, wherein the compound is 3-((1,2,3,4-tetrahydro-6,7-dimethoxyisoquinoline-2-yl)methyl)-4-hydroxyquinoline-2-carboxylic acid.

15. The compound according to claim 3, wherein the compound is N-(2-(dimethyl amino)ethyl)-4-hydroxy-3-(morpholinomethyl)quinoline-2-carboxylic acid amide.

16. The compound according to claim 3, wherein the compound is 3-((diethyl amino)methyl)-4-hydroxy-N-(2-(pyrrolidin-1-yl)ethyl)quinoline-2-carboxylic acid amide.

17. The compound according to claim 3, wherein the compound is 4-hydroxy-N-(2-(pyrrolidin-1-yl)ethyl)-3-((pyrrolidin-1-yl)methyl)quinoline-2-carboxylic acid amide.

18. The compound according to claim 3, wherein the compound is 4-hydroxy-3-(morpholinomethyl)-N-(2-(pyrrolidin-1-yl)ethyl)quinoline-2-carboxylic acid amide.

* * * * *